US012779096B2

(12) United States Patent
Salama et al.

(10) Patent No.: US 12,779,096 B2
(45) Date of Patent: Nov. 3, 2026

(54) METHOD FOR MAKING NANOCOMPOSITE FILM

(71) Applicant: Imam Abdulrahman Bin Faisal University, Dammam (SA)

(72) Inventors: Khaled Fikry Salama, Dammam (SA); Arwa Abdulrahman Al Thumari, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 588 days.

(21) Appl. No.: 18/463,335

(22) Filed: Sep. 8, 2023

(65) Prior Publication Data

US 2023/0414841 A1 Dec. 28, 2023

Related U.S. Application Data

(62) Division of application No. 17/088,170, filed on Nov. 3, 2020, now Pat. No. 11,850,312.

(51) Int. Cl.
*A61L 31/08* (2006.01)
*A61L 31/02* (2006.01)
(Continued)

(52) U.S. Cl.
CPC .......... *A61L 31/088* (2013.01); *A61L 31/028* (2013.01); *A61L 31/124* (2013.01); *A61L 31/16* (2013.01);
(Continued)

(58) Field of Classification Search
CPC .... A61L 31/088; A61L 31/028; A61L 31/124; A61L 31/16; A61L 2400/12; A61L 2420/06; A61L 2420/08
See application file for complete search history.

(56) References Cited

U.S. PATENT DOCUMENTS 5,824,267 A * 10/1998 Kawasumi ............ A01N 25/34 424/618
2016/0137804 A1* 5/2016 Van der Ven ............ C08J 9/14 428/318.6

FOREIGN PATENT DOCUMENTS

CN 102504318 B 2/2014
CN 105602062 A 5/2016
(Continued)

OTHER PUBLICATIONS

Barani et al., Increasing the shelf life of pikeperch (*Sander lucioperca*) fillets affected by low-density polyethylene/Ag/TiO2 nanocomposites experimentally produced by sol-gel and melt-mixing methods, Jan. 2018, International Journal of Food Properties, vol. 21, p. 1923-1936 (Year: 2018).*

(Continued)

*Primary Examiner* — Mark Eashoo
*Assistant Examiner* — Caitlin Norine Illing
(74) *Attorney, Agent, or Firm* — Oblon, McClelland, Maier & Neustadt, L.L.P.

(57) ABSTRACT

A health care and/or entertainment device protective film may be configured to contact human skin, e.g., to limit the transmission of infection by bacteria, fungi, protozoa, prions, and/or viruses. The film may be formed as a nanocomposite film including at least 75 wt. %, relative to total organic matrix weight, of polyethylene, silver particles, and $TiO_2$ particles, wherein the silver particles and $TiO_2$ particles are distributed within and/or on an outer surface of the polyethylene, wherein the silver particles have a size of 1 to 1,000 nm, and wherein the $TiO_2$ particles have a size of 1 to 50 nm. Such films may be applied to health care and/or entertainment devices, including virtual reality googles.

14 Claims, 18 Drawing Sheets

(51) Int. Cl.
*A61L 31/12* (2006.01)
*A61L 31/16* (2006.01)

(52) U.S. Cl.
CPC ....... *A61L 2400/12* (2013.01); *A61L 2420/06* (2013.01); *A61L 2420/08* (2013.01)

(56) References Cited

FOREIGN PATENT DOCUMENTS

| | | | | | |
|---|---|---|---|---|---|
| CN | 106519389 | A | | 3/2017 | |
| CN | 107118460 | A | | 9/2017 | |
| CN | 107383542 | A | | 11/2017 | |
| CN | 105968489 | B | | 8/2018 | |
| EP | 3929236 | A1 | * | 12/2021 | ............... C08K 3/08 |
| WO | WO-2018131055 | A1 | * | 7/2018 | ............. A01N 59/16 |

OTHER PUBLICATIONS

Linseis, Low density polyethylene (LDPE): A summary, archived Oct. 2024 (Year: 2026).*
Merck, Titanium(IV) Oxide, product listing, accessed 2026 (Year: 2026).*
Zouch Converters, Closed Cell Polyethylene Foam for Food Contact Applications, Oct. 22, 2018 (Year: 2018).*
Nafiseh Hosseini Nasab, et al., "A study on properties of polymeric films incorporated with silver-coated $TiO_2$ nano particles", The 21st International Electronic Conference on Synthetic Organic Chemistry, Nov. 3, 2017, 7 pages.
Somayeh Lotfi, et al., "The effect of silver nanocomposite packaging based on melt mixing and sol-gel methods on shelf life extension of fresh chicken stored at 4° C.", Journal of Food Safety, vol. 39, Issue 3, Jan. 20, 2019, 2 pages (Abstract only).
Gabriel Molina de Olyveira, et al., "Novel LDPE/EVA Nanocomposites with Silver/Titanium Dioxide Particles for Biomedical Applications", Journal of Materials Science and Engineering B, vol. 1, Sep. 2011, pp. 516-522.
Amal M. Metak, "Effects of Nanocomposite Based Nano-Silver and Nano-Titanium Dioxide on Food Packaging Materials", International Journal of Applied Science and Technology, vol. 5, No. 2, Apr. 2015, pp. 26-40.
Shahab Ansari Amin, et al., "Synthesis of $TiO_2$—Ag nanocomposite with sol-gel method and investigation of its antibacterial activity against *E. coli*", Powder Technology, vol. 196, 2009, pp. 241-245.

* cited by examiner

METHOD FOR MAKING NANOCOMPOSITE FILM

CROSS-REFERENCE TO RELATED APPLICATIONS

The present application is a division of U.S. application Ser. No. 17/088,170, pending, having a filing date of Nov. 3, 2020.

BACKGROUND OF THE INVENTION

Field of the Invention

The present disclosure relates to films (foils) of polyethylene, particularly LDPE, containing silver and titania nanoparticles, for example, for covering or protecting medical, dental, or other healthcare equipment, particularly virtual reality instrumentation, and methods of making and using such films.

Description of the Related Art

Amongst the most common causes of pain include chronic illness, accidents, surgery, advanced cancer, lower back problems, arthritis, shingles, headaches, and fibromyalgia. Many patients enduring such pain have difficulties obtaining adequate medication to control their pain. Virtual reality (also referred to as VR) is a medical tool which can be used to draw a patient's attention away from the patient's mental processing, thereby decreasing the amount of pain consciously experienced by the patient. Virtual reality has also been found to be effective in reducing reported pain and distress in patients undergoing burn wound care, chemotherapy, dental procedures, venipuncture, and prolonged hospital visits. Virtual reality may change how the brain physically registers pain, not just the perception of pain stimuli, and thus may offer new avenues for pain alleviation.

Several studies have found virtual reality to be effective in reducing procedural pain, even in patients subjected to extremely painful procedures, such as those with burn injuries undergoing wound care and physical therapy. In different settings, including chemotherapy visits, virtual reality has been reported to reduce cancer-related symptoms, and its side effects have been to be found to be mild and infrequent.

Developments in the nanotechnology field and their applications to the field of medicine and pharmaceuticals in the twentieth century have led to the provision of solutions for many problems. Nanotechnology pertains to materials having morphological features on nanometer scale(s), bringing about a standard class of materials with enhanced properties for an extensive variety of uses.

Sharing or using virtual reality equipment between patients or other users can result in cross bacterial infection As a typical minimum use time for virtual reality is 15 minutes and ordinary disinfectants in application and misuse typically provide less that 100% decontamination, especially with multi resistant bacterial strains in patients in isolation wards in hospitals, the risks of infection are high. Prior to patient use, fabric surfaces of virtual reality devices are typically cleaned with 70% alcohol (isopropanol or ethanol) or hydrogen peroxide wipes, and the glass lenses or plastic are typically cleaned with an alcohol-based lens cleaner.

Disposable fabric covers have been used in the art for virtual reality goggles for each individual user, for example, with fitted head caps on patients, to minimize direct contact with the device as recommended by standard infection control protocols. It has been recommended that each patient discard the disposable head cap, fabric cover, and foam backing from each virtual reality device used, with each patient ideally having his or her own headset and fabric covers. However, such an approach is not particularly cost-effective, presently costing about $19 to $29 US for each fabric cover, nor is this practice particularly environmentally friendly.

The use of virtual reality devices in a hospital or health care setting has typically required meticulous cleaning between patients, application of fresh liners for each use, and provision of a head cap to minimize infection risk. Such hygienic precautions and technical shortcomings may unduly limit the scalability and/or applicability of virtual reality equipment, therefore there is a need in the art for more efficient, cost-effective, and/or improved approaches for the form factors of current virtual reality devices and other health care equipment.

Silver nanoparticles (also referred to as "Ag NPs") and titanium oxide nanoparticles (also referred to as "$TiO_2$ NPs") are the two types of nanoparticles that are most widely used as antimicrobial agents. Combinations of silver nanoparticles and titanium oxide nanoparticles with polyethylene made in a molten state or during melting may enhance the photocatalytic property of $TiO_2$ by promoting electron-hole separation and introducing more surface area absorption. The absorption of visible light by silver nanoparticles on the surface of materials could also stimulate electron transfer to titanium oxide nanoparticles, resulting in charge separation and activation of the titanium oxide nanoparticles by such absorbed visible light.

CN 102504318 B to Xuhong (Xuhong) discloses medical devices such as a silver-loaded nano titanium dioxide ($TiO_2$) medical polyethylene tracheal intubation catheter with a modified surface. Xuhong uses an irradiation grafting reaction to modify the surface of the medical polyethylene intubation, involving: activating the surface of a base material, preparing a silver-loaded nano-T102 hydrophobic antibacterial masking liquid, and antimicrobial modifying the base material surface. Xuhong's material can reduce diseases associated with retention of the tracheal intubation catheter, prolonging the catheter retention time, and is suitable for clinical application. Xuhong's particles have a silane/ester polymeric coating applied the surface. Xuhong's silver and $TiO_2$ are not homogenously distributed throughout a polyethylene matrix, and Xuhong does not disclose an antibacterial protective film for a medical or entertainment device, configured to contact epidermis/skin.

CN 107118460 A by Cui (Cui) discloses a sterilized glove and its preparation, comprising as raw materials by weight: 1 to 5% of an additive and 95 to 99% of a main material, the additive comprising: 20 to 40% of nano-sized silver, 5 to 10% of nano-sized $ZnO_2$, 5 to 10% of nano-sized $TiO_2$, 5 to 10% of nano-sized silver nitrate, 20 to 30% of an adhesive, and 5 to 10% of a stabilizer. Cui's glove has lasting and stable antibacterial and bactericidal effects, and the glove can be reused. Cui's main material comprises polyvinyl chloride, polyurethane, polypropylene random copolymer, polypropylene, ethylene-vinyl acetate copolymer, or acrylonitrile-styrene-butadiene copolymer. Cui's binder is an amine resin, and Cui does not disclose a polyethylene matrix.

CN 105968489 B to Luo et al. (Luo) discloses a preparation of a polyethylene antimicrobial packaging film, including (by weight): adding 0.3 to 1.0 part of silver-loaded nanotitania into 100 parts of polyethylene resin; adding 0.06 to 0.24 part of a first antioxidant and 0.04 to 0.16 parts of a second antioxidant; mixing in a high-speed mixer; granulating, drying, and blowing a film to prepare the polyethylene antimicrobial packaging film. Luo's silver-ammonia ions form a strong interaction with the titania surface via pH modulation, and the silver-ammonia ions are reduced with a loquat fruit aqueous extract. Luo requires particular antioxidants, such as n-octadecyl-β-(4-hydroxy-3,5-di-tert-butylphenyl)propionate and tris(2,4-di-tert-butylphenol) phosphite, Luo uses only 0.3, 0.5, and 1 wt. % titania-silver nanoparticles (containing 0.5 wt. % silver), and Luo does not describe health care or entertainment device covers.

CN 106519389 A by Jin (Jin) discloses a nanometer packaging material and its preparation, involving: (1) mixing wollastonite and sepiolite, adding the mixture into a grinding machine, grinding the mixture, and sieving the ground mixture at 200 mesh to obtain a powder mixture; (2) adding nanometer Ag powder, nanometer $TiO_2$, chitosan, LDPE, an PE-VA, oils, silane coupling agents, greases, and antioxidant, and mixing the materials at high speed; (3) extruding and granulating; and (4) cooling and blow molding through a blowing machine. Jin uses, relative to total material weight, 1.7 to 6.1 wt. % Ag, 9 to 22 wt. % $TiO_2$, and 36 to 56 wt. % LDPE. Jin does not disclose medical or entertainment device protective film, nor contacting the film with human skin.

CN 105602062 A by Zhou et al. (Zhou) discloses a $TiO_2$-PE composite plastic, comprising by weight: 100 to 150 parts of PE, 10 to 30 parts of an antibacterial agent, 20 to 50 parts of nano $TiO_2$ powder, 10 to 25 parts of PVA, 5 to 10 parts of PE wax, 2 to 10 parts of a dispersant, 3 to 5 parts of a photoinitiator, and 3 to 10 parts of a photosensitizer. Zhou's PE wax is mainly distributed on a first surface layer, and the PVA is mainly distributed on a second surface layer, of the composite plastic. Zhou's antibacterial agent may be silver or zinc, present from 3.7 to 17.3 wt. % of the total weight of the material, while Zhou's $TiO_2$ is 7.69 to 27.3 wt. % of the total material. Zhou's polyethylene is at most 73.9 wt. % of the total weight of the composition, and Zhou does not describe covers for medical or entertainment devices.

CN 107383542 A by Cheng et al. (Cheng) discloses a mold-proof plastic packaging bag and its preparation from, by weight: 30 to 65 parts (i.e., 21.6 to 53.1 wt. %) of polyethylene resin, 10 to 25 parts (i.e., 6.5 to 25.5 wt. %) of nano-silver, 10 to 25 parts (i.e., 9.4 to 26.9 wt. %) of nano-titania, 5 to 15 parts of coupling agent, 3 to 8 parts of plasticizer, 5 to 8 parts of antistatic agent, 2 to 8 parts of stabilizer, and 8 to 20 parts of filler. Cheng uses coupling agents, plasticizers, antistatic agents, stabilizers, and fillers, and Cheng does not describe applications for health care or entertainment device.

The conference paper from The 21st International Electronic Conference on Synthetic Organic Chemistry entitled "A study on properties of polymeric films incorporated with silver-coated $TiO_2$ nano particles," by Nasab et al. (Nasab), discloses LDPE nanocomposite films containing different concentrations of silver nanoparticles and $TiO_2$, manufactured via extrusion. Nasab reports silver/$TiO_2$ surfaces provide visible light photo catalysis, biological compatibility, and antimicrobial activity. Nasab uses 4 wt. % of a paraffin wax as a compatibilizer and requires extrusion, and Nasab does not disclose any health care or entertainment device application for its film, nor direct contact of the material with skin.

*J. Food Safety* 2019, 39(3), e12625 by Lofti et al. (Lofti) discloses films produced using different proportions of polyethylene containing silver, clay, and titanium dioxide nanoparticles. Lofti investigates eradication of *Staphylococcus aureus* and *Escherichia coli*, and reports that a film containing 5% silver nanoparticles and 5% titanium dioxide nanoparticles to have the highest antimicrobial property, characterizing it as an ideal cover for food products. Lofti reports that the nanocomposite can preserve chicken meat for 5 days at 4° C., and inhibited growth of both types of bacteria. Lofti describes no films for health care and/or entertainment instrumentation, nor directly contacting the epidermis with the film.

*J. Mater. Sci. Eng. B* 2011, 1, 516-522 by Olyveira et al. (Olyveira) discloses antimicrobial nanocomposites with titanium dioxide (P-25) and silver in PE. Olyveira makes nanocomposites by processing LDPE/EVA with Ag nanoparticles on $TiO_2$ particles as an inorganic carrier substance, and dispersing the Ag/$TiO_2$ nanoparticles at 0.5, 0.8, and 1 wt. % in molten LDPE/ethylene vinyl acetate copolymer (EVA)-(50% w/w). Olyveira reports that incorporation of silver/titanium dioxide nanoparticles on its nanocomposites showed uniform distribution of Ag on $TiO_2$ particles and antimicrobial properties. Olyveira fails to describe using the films with health care and entertainment devices.

*Int. J. Appl. Sci. Techn.* 2015, 5(2), 26-40 by Metak (Metak) discloses commercial antimicrobial nano-silver food packaging containers incorporating 1 wt. % nano-silver and 0.1% titanium dioxide ($TiO_2$) nanoparticles into polymeric materials formed into food containers. Metak's containers showed antibacterial properties against *S. aureus* and *E. coli*, but Metak does not address health care or entertainment devices, nor contact with skin.

In light of the above, a need remains for films/foils useful in covering health care and/or entertainment equipment coming into contact with human skin, such as medical, dental, orthodontal, veterinary, and/or visualization equipment, particularly for covering contact surfaces of virtual reality devices, such as goggles, and methods of making and using such films/foils.

SUMMARY OF THE INVENTION

Aspects of the invention provide health care and/or entertainment device protective films configured to contact human skin, the films comprising, as a nanocomposite: at least 75 wt. %, relative to total organic matrix weight, of polyethylene; silver particles; and $TiO_2$ particles, wherein the silver particles and $TiO_2$ particles are distributed within and/or on an outer surface of the polyethylene, wherein the silver particles have a size of 1 to 1,000 nm, and wherein the $TiO_2$ particles have a size of 1 to 50 nm. Inventive films and/or methods may be modified with any permutation of the features described herein, particularly the following.

Inventive films may comprise, based on total film weight: 1 to 5 wt. % of the silver particles; and/or 1 to 10 wt. % of the $TiO_2$ particles. The thickness of the outer surface comprising the silver and $TiO_2$ particles may be in a range of from 0.025 to 25 m.

The polyethylene may be LDPE and/or may be present in an amount of at least 97.5 wt. % relative to the relative to total organic matrix weight. The polyethylene may have a melting point in a range of from 90 to 125° C. The polyethylene may have a density in a range of from 0.9 to 0.99 g/cm$^3$. The polyethylene may be foamed or in foam form.

The $TiO_2$ particles may have an average longest dimension of no more than 25 nm. The $TiO_2$ particles may have an average sphericity of at least 0.91.

Inventive films may comprise no more than 2 wt. % of the silver particles.

Inventive films may be configured to conform to a cushion on goggles contacting the skin.

Aspects of the invention provide methods for making any permutation of the inventive nanocomposite film described herein. Such methods may comprise: dispersing and thereby mixing polyethylene, the silver particles, and the $TiO_2$ particles in a solvent to form a dispersion; drying to form a dry mixture; and/or melt mixing the dry mixture to form the nanocomposite.

Inventive methods may further comprise, prior to the dispersing: suspending the polyethylene in a first solvent for at least 5 minutes. The suspending of the polyethylene may take place for up to 12 hours.

The first solvent may comprise an alcohol, and/or the first solvent may comprise at least 75 wt. % of methanol, based on total solvent weight.

Inventive methods may further comprise, prior to the dispersing: forming the silver particles in situ by reducing a silver precursor with a reducing agent.

The melt mixing may comprise heating at a temperature in a range of 10% of a melting point of the polyethylene. The melt mixing may comprise heating at a temperature in a range of from 100 to 115° C.

Aspects of the invention provide methods of reducing infection transmission, the method may comprise: contacting a health care and/or entertainment device comprising any permutation of the inventive nanocomposite film described herein, with a first portion of skin of a first person, on the film; and contacting the film with a second portion of skin of a second person.

Aspects of the invention provide health care and/or entertainment devices comprising any permutation of the inventive nanocomposite film described herein, wherein the nanocomposite film is located on a portion of the health care and/or entertainment device configured to contact skin.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
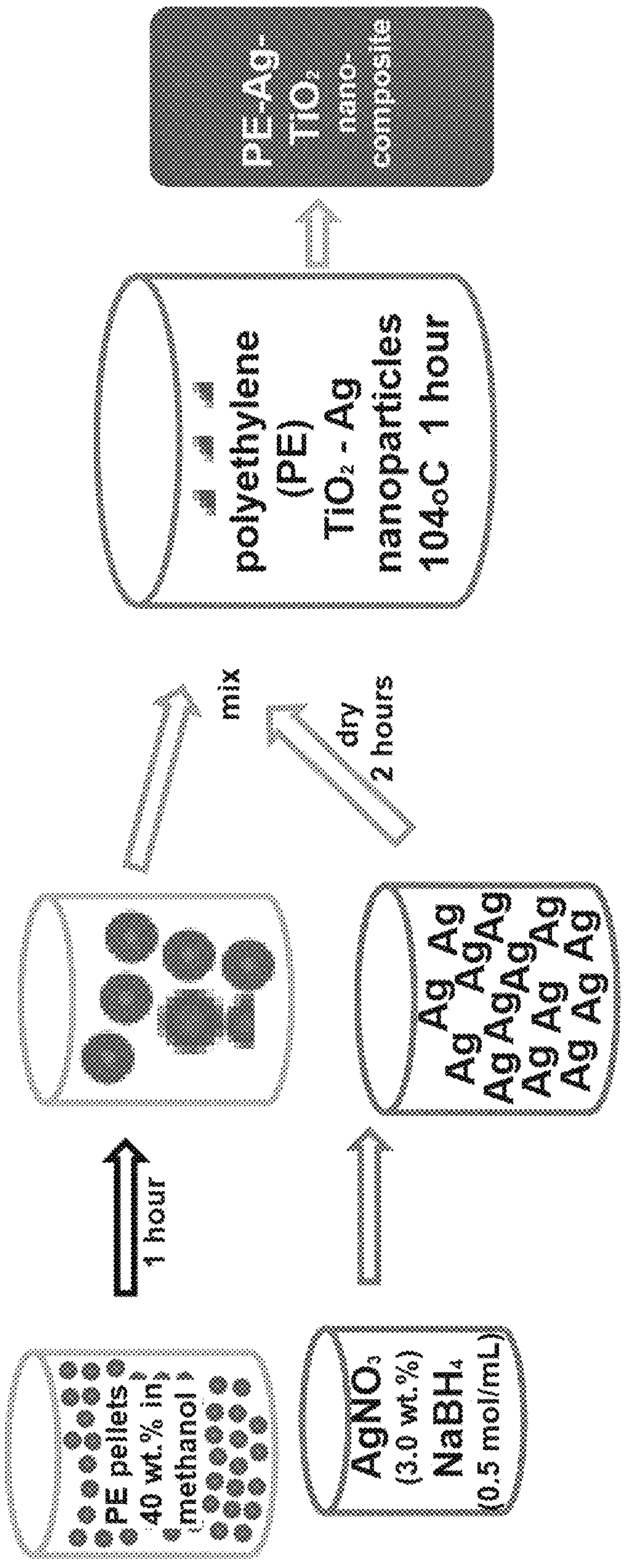
FIG. 1 shows a representation of the synthesis of an exemplary silver nanoparticles containing polyethylene material.

Aspects of the invention provide health care and/or entertainment device protective films configured to contact human skin, particularly the epidermis such as on non-internal surfaces of the face, chest, back, legs, pelvis, arms, shoulder, neck, etc., though typically not within the mouth, nose, ears, rectum, vagina, or other natural or synthetic orifice. With contact, i.e., contacting the skin, a direct contact of the epidermis to the film is contemplated, without intervening layers, oils, salves, ointments, or the like (though it excluding medical or therapeutic skin treatment formulations is unnecessary). Such films may comprise, as a nanocomposite: at least 75, 80, 85, 90, 91, 92, 92.5, 93, 94, 95, 96, 97, 97.5, 98, 99, 99.1, 99.5, or 99.9 wt. %, relative to total organic matrix weight (typically substantially or only containing polymers, but measured as any organic contents, e.g., polymers and small molecules), of polyethylene; silver particles; and $TiO_2$ particles, wherein the silver particles and $TiO_2$ particles are distributed within and/or on an outer surface of the polyethylene, wherein the silver particles have a size of 1 to 1,000 nm (e.g., at least 1, 1.5, 2, 2.5, 3, 4, 5, 7.5, 10, 12.5, or 15 nm and/or up to 1,000, 750, 500, 400, 350, 300, 250, 225, 200, 175, 150, 125, 100, 90, 80, 75, 70, 65, 60, 55, 50, 45, 40, 35, or 30 nm), and wherein the $TiO_2$ particles have a size of 1 to 50 nm (e.g., at least 1, 1.25, 1.5, 1.75, 2, 2.25, 2.5, 2.75, 3, 3.5, 4, 4.5, 5, 6, 7, 7.5, 8, 9, or 10 nm and/or up to 50, 47.5, 45, 42.5, 40, 37.5, 35, 32.5, 30, 27.5, 25, 22.5, 20, 17.5, 15, 12.5, or 10 nm).

The polyethylene may be a low-density polyethylene (LDPE) and/or may have a density range of 0.917 to 0.930 g/cm$^3$, e.g., at least 0.917, 0.918, 0.919, 0.92, 0.921, 0.922, 0.923, 0.924, 0.925, 0.926, 0.927, or 0.9275 g/cm$^3$ and/or up to 0.930, 0.929, 0.928, 0.9275, 0.927, 0.9265, 0.926, 0.925, 0.924, 0.923, 0.922, 0.921, or 0.92 g/cm$^3$. The LDPE may have 2±0.01, 0.025, 0.05, 0.075, 0.1, 0.15, 0.2, 0.25, 0.33, or 0.4% of the carbon atoms containing branching. The LDPE may be a linear low density polyethylene (LLDPE) and/or an LLDPE manufactured using metallocene catalysts, i.e., mLLDPE. Relevant polyethylenes may be made with transition metal catalysts, Ziegler catalysts, or Philips type catalysts. Relevant polyethylenes, beyond ethylene, may include up to 5, 4.5, 4, 3.5, 3.33, 3, 2.75, 2.5, 2.25, 2, 1.75, 1.5, 1.25, 1, 0.9, 0.8, 0.75, 0.7, 0.6, 0.5, 0.4, 0.33, 0.3, 0.25, 0.2, 0.15, 0.1 mol. % further monomers, including, e.g., propylene, 1-butene, and/or isobutene. The polyethylene may have a melting point in a range of from 90 to 125° C., e.g., at least 90, 91, 92, 92.5, 93, 94, 95, 96, 97, 97.5, 98, 99, 100, 101, 102, 102.5, 103, 104, or 105° C. and/or 125, 122.5, 120, 119, 118, 117.5, 117, 116, 115, 114, 113, 112.5, 112, 111, 110, 109, 108, 107.5, 107, 106, or 105° C.

Inventive films may comprise, based on total film weight: 1 to 5 wt. % of the silver particles, e.g., at least 0.5, 0.75, 1, 1.25, 1.5, 1.75, 2, 2.25, 2.5, 2.75, or 3 wt. % Ag and/or up to 5, 4.75, 4.5, 4.25, 4, 3.75, 3.5, 3.25, 3, 2.75, 2.5, 2.25, or 2 wt. % Ag; and/or 1 to 10 wt. % of the $TiO_2$ particles, e.g., at least 1, 1.5, 2, 2.5, 3, 3.5, 4, 4.5, 5, 5.5, 6, 6.5, 7, or 7.5 wt. % $TiO_2$ and/or up to 10, 9.5, 9, 8.5, 8, 7.5, 7, 6.5, 6, 5.5, 5, 4.5, 4, 3.5, 3, or 2.5 wt. % $TiO_2$.

The silver and titania nanoparticles may form an outer layer on the nanocomposite, i.e., upon the polyethylene matrix (which does not necessarily exclude, but may exclude for certain applications, that particles be within the polymer matrix). The thickness of the outer surface comprising the silver and $TiO_2$ particles may be in a range of from 0.025 to 25 m, e.g., 0.025, 0.033, 0.05, 0.075, 0.1, 0.25, 0.5, 0.75, 1, 2, 2.5, 3.33, 5, 7.5, or 10 μm and/or up to 25, 24, 23, 22, 21, 20, 19, 18, 17.5, 17, 16, 15, 12.5, 10, 7.5, 7, 6, 5, 4, 3, or 2.5 μm. The $TiO_2$ particles may have an average longest dimension (or in the context of spheroids, diameter) of no more than 25, 24, 23, 22.5, 22, 21, 20, 19, 18, 17.5, 17, 16, 15, 14, 13, 12.5, 12, 11, 10, 9, 8, 7.5, 7, 6, or 5 nm. The $TiO_2$ particles and/or Ag particles may have an average sphericity of at least 0.91, 0.915, 0.92, 0.925, 0.93, 0.935, 0.94, 0.945, 0.95, 0.955, 0.96, 0.965, 0.97, 0.975, 0.98, 0.985, or 0.99. Inventive films may comprise no more than 2, 1.95, 1.9, 1.85, 1.8, 1.75, 1.7, 1.65, 1.6, 1.55, or 1.5 wt. % of the silver particles, and/or at least 1, 1.1, 1.15, 1.2, 1.25, 1.3, 1.35, 1.4, 1.45, or 1.5 wt. %.

Figure 6:
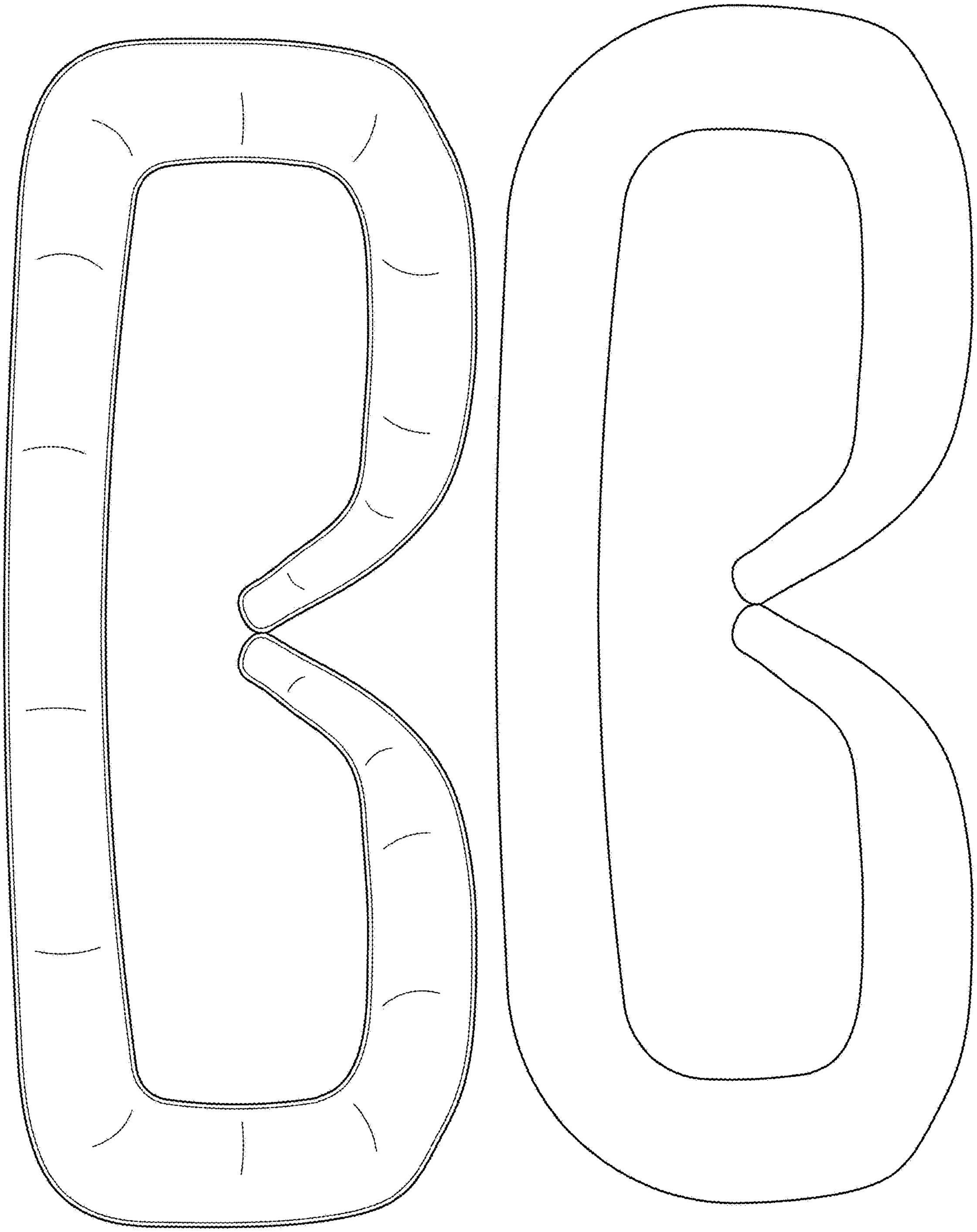
FIG. 6 shows a first exemplary antimicrobial film/membrane in the form of a virtual reality goggle protective cover sample containing the nanocomposite polyethylene-$TiO_2$—Ag nanoparticles.
Figure 7:
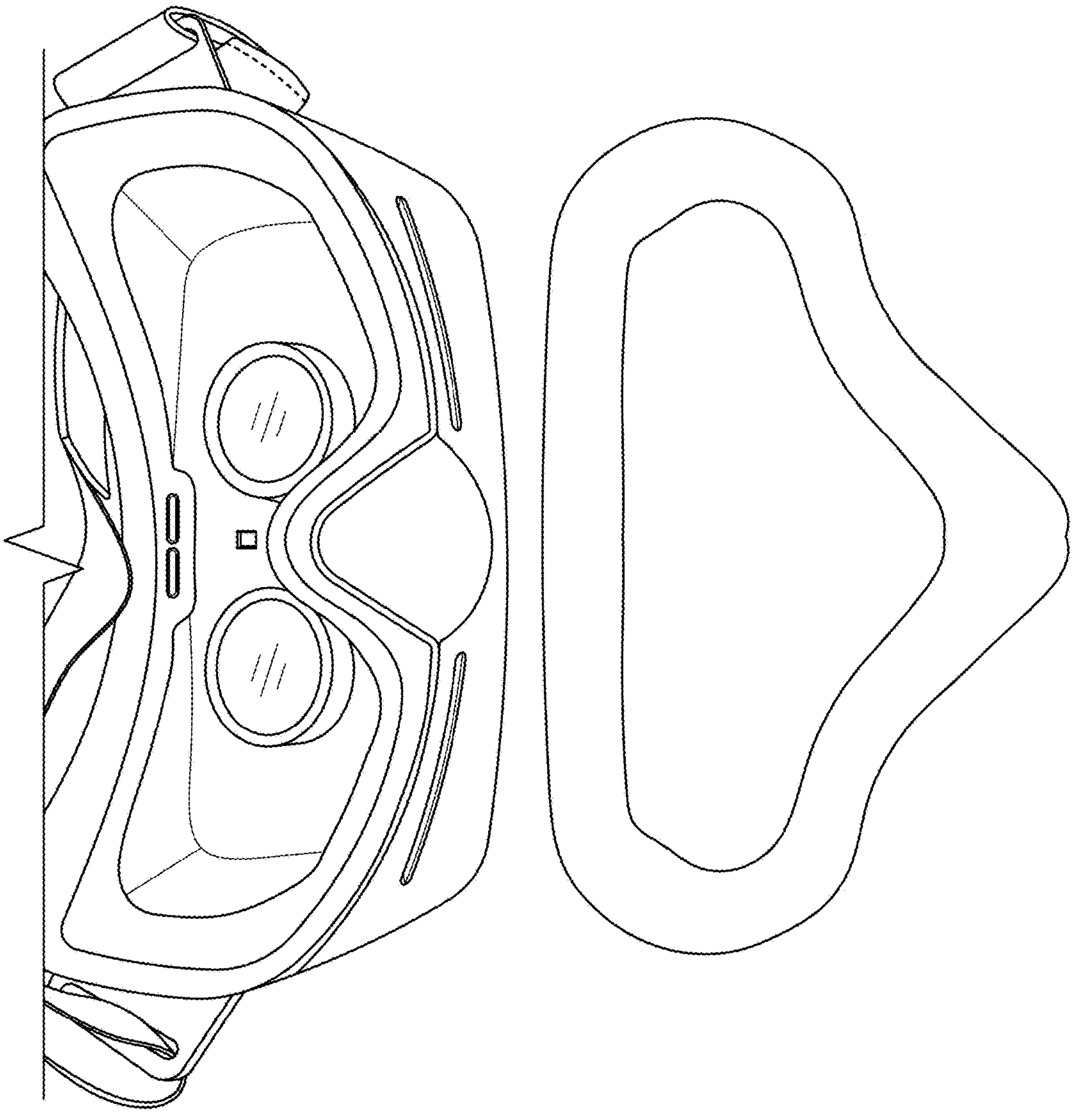
FIG. 7 shows a second exemplary antimicrobial film/membrane in the form of a virtual reality goggle protective cover sample containing the nanocomposite polyethylene-$TiO_2$—Ag nanoparticles.

Inventive films may be configured to conform to a cushion on goggles contacting the skin, as seen, for example in FIGS. 6 and 7. Inventive films may be cut to form around the perimeter of devices, including empty spaces within otherwise contiguous film surfaces. Inventive films include contoured, curved, elliptical, and/or rounded portions (with radii of e.g., 1, 1.5, 2, 2.5, 3, 3.5, 4, 4.5, 5, 6, 7, 7.5, or 10 cm), and/or may contain linear or bar-shaped portions and/or angles of 30, 45, 60, 90, 115, 120, 135, 150, and/or 165°.

The nanocomposite may be a foamed film or slab. The thickness of the foam film may be in a range of from 0.05 to 3 cm, e.g., at least 0.05, 0.1, 0.15, 0.2, 0.25, 0.33, 0.4, 0.5, 0.75, 1, 1.5, or 2 cm and/or up to 3, 2.75, 2.5, 2.25, 2, 1.75, 1.67, 1.5, 1.33, 1.25, 1.125, 1, 0.95, 0.9, 0.85, 0.8, or 0.75 cm, and have a density ranging from 0.025 to 0.95 g/cm$^3$, e.g., at least 0.025, 0.03, 0.035, 0.04, 0.045, 0.05, 0.055, 0.06, 0.065, 0.07, or 0.075 g/cm$^3$ and/or up to 0.95, 0.9, 0.85, 0.8, 0.75, 0.7, 0.65, 0.6, 0.55, 0.5, 0.45, 0.4, 0.35, 0.3, 0.25, 0.2, 0.15, 0.145, 0.14, 0.135, 0.13, 0.125, 0.12, 0.115, 0.11, 0.105, or 0.1 g/cm$^3$. Although porous, the foamed film may prevent the passage of liquid, such as water, alcohol, and/or oil, or reduce the passage of any of these up to 10, 15, 20, 25, 33, 40, 50, 55, 60, 65, 70, 75, 80, 85, 90, 92.5, 95, 97.5, 98, 99, 99.5, or 99.9%. Preferably, the foamed film is in the form of a sandwich structure having outer layers (skins) made of continuous non-porous nanocomposite covering at least an inner portion of a foamed composite material. All of the outer layers of film and/or the inner foam film may comprise the nanocomposite. As such, the nanocomposite film may have a greater resistance to colonization by bacteria that may be transmitted, for example, by perspiration or other bodily fluids from an individual that is handling a medical device or is exposed to contact with a surface that might otherwise be infectious.

The foamed nanocomposite may be a padding for a health care and/or entertainment device, such as the frame of a VR goggle set, or of a glucose measurement device, or of a thermometer, or the like. Foamed materials may be cross-linked, e.g., at 1 cross-link per 1000, 750, 500, 250, 200, 150, 100, 90, 80, 70, 60, 50, 40, 30, 25, 20, 15, or 10 monomers.

Aspects of the invention may provide virtual reality goggle devices, comprising: any permutation of the inventive nanocomposite film; and a flexible portion upon with the nanocomposite film rests opposite a surface contacting a hard plastic frame. The flexible portion may be an elastomeric and/or foamed material, wherein the elastomer and/or foam may include the titania and/or silver particles in any form described herein and/or the polyethylene. The flexible portion may be integral with the film. The goggle may contain air or a gas, surrounded by the nanocomposite film in a balloon-type arrangement. The goggle may include a polyurethane foam, closed or open cell, for the flexible portion, or a silicon rubber, a nitrile rubber, an SBR, butadiene rubber, neoprene rubber, natural rubber, or the like. Inventive films may be similarly used on telescopes, binoculars, microscopes, and other viewing instruments. Inventive films may be used on a glove-box. The film may be a part of a multi-layered film arrangement, wherein the user can tear off and discard the outermost layer (e.g., after a use involving contacting the skin). The films may be present as “pads” of multiple layers of the film.

Aspects of the invention provide methods for making any permutation of these inventive nanocomposite films, e.g., comprising: dispersing and thereby mixing polyethylene (which may be beads, pellets, spheroids, cubes, cut strings, or any other embodiment of synthetically or commercially available polymer), the silver particles, and the $TiO_2$ particles in a solvent to form a dispersion; drying to form a dry mixture; and/or melt mixing the dry mixture to form the nanocomposite. “Melt mixing” is meant to encompass any form of mixing the materials at a temperature around the melting point, particularly at or above the melting point, of the matrix. The mixing in the method may include stirring, shaking, periodically agitating, rotating, etc., or combinations of these. The melt mixing may comprise heating at a temperature in a range of 25, 20, 15, 12.5, 10, 9, 8, 7.5, 7, 6, 5, 4, 3, 2.5, 2, 1, or 0.5% of a melting point of the polyethylene. The melt mixing may comprise heating at a temperature in a range of from 100 to 115° C., e.g., at least 100, 100.5, 101, 101.5, 102, 102.5, 103, 103.5, 104, 104.5, or 105° C. and/or up to 115, 114.5, 114, 113.5, 113, 112.5, 112, 111.5, 111, 110.5, 110, 109.5, 109, 108.5, 108, 107.5, 107, 106.5, 106, 105.5, or 105° C. (or any aforementioned temperature or range).

Inventive methods may further comprise, prior to the dispersing: suspending the polyethylene in a first solvent for at least 5 minutes, e.g., at least 5, 10, 15, 20, 30, 45, 60, 90, or 120 minutes and/or (though the solvent treatment does not need to be limited) up to 12, 11, 10, 9, 8, 7, 6, 5, 4, 3, 2, 1.5, or 1 hours. The first solvent may be a mixture of 1, 2, 3, 4, 5, or more solvents, or may be a single solvent. The first solvent comprise (e.g., 50, 60, 70, 75, 80, 85, 90, 91, 92, 92.5, 93, 94, 95, 96, 97, 97.5, 98, 99, 99.1, 99.5, or 99.9 wt. %) an alcohol, and/or the first solvent may comprise at least 75, 80, 85, 90, 91, 92, 92.5, 93, 94, 95, 96, 97, 97.5, 98, 99, 99.1, 99.5, or 99.9 wt. % of methanol, based on total solvent weight. The first solvent may (further) comprise pyridine, N,N-dimethylformamide (DMF), N,N-dimethylacetamide, N-methyl pyrrolidone (NMP), hexamethylphosphoramide (HMPA), dimethyl sulfoxide (DMSO), acetonitrile, tetrahydrofuran (THF), 1,4-dioxane, dichloromethane, chloroform, carbon tetrachloride, dichloroethane, acetone, ethyl acetate, pet ether, pentane, hexane(s), cyclohexane, decane(s), decalin, THF, dioxane, benzene, toluene, xylene(s), o-dichlorobenzene, diethyl ether, methyl t-butyl ether, diisopropyl ether, ethylene glycol, methanol, ethanol, isopropanol, propanol, n-butanol, and/or water.

Inventive methods may further comprise, prior to the dispersing: forming the silver particles in situ by reducing a silver precursor, such as a silver ion with a nitrate, halide (e.g., chloride, bromide, iodide), sulfate, phosphate, chlorate, perchlorate, bromate, perbromate, periodate, etc., or mixtures thereof) with a reducing agent, such as a borohydride (sodium and/or lithium), an aluminum hydride (sodium and/or lithium, SMEAH), Raney Ni, Clemenson agents (Zn, Sn, etc.), formates, etc.

Aspects of the invention provide methods of reducing (e.g., to 99, 97.5, 95, 92.5, 90, 85, 80, 75, 70, 65, 60, 50% or less of use without the films) infection transmission, the method may comprise: contacting a health care and/or entertainment device comprising any permutation of the inventive nanocomposite film described herein, with a first portion of skin of a first person, on the film; and contacting the film with a second portion of skin of a second person. The use of the protectively coated device could be for 1, 2, 3, 4, 5, or more patients. The protective films/sheets could be discarded on some regular interval, e.g., daily, every other or third or fourth day, weekly, monthly, upon ripping, or otherwise. The infective agent may be bacterial, fungal, protozoal, or otherwise.

Aspects of the invention provide health care and/or entertainment devices comprising any permutation of the inventive nanocomposite film described herein, wherein the nanocomposite film is located on a portion of the health care and/or entertainment device configured to contact skin. Relevant devices may be virtual reality goggles, seats (head rests, arm rests), operating tables, birthing tables, examination tables, dental trays, gloves, mouth masks, gas masks, self-contained suits, or the like. The film may cover 5, 10, 20, 25, 33, 50, 67, 75, 85, or 100% of the surface of such health care and/or entertainment devices, particularly all of the skin contacting surfaces.

Inventive materials can avoid the use of radical (or photo) initiators, such as azobisisobutyronitrile, a diaryliodonium salt, a triarylsulfonium salt, in the silver and/or $TiO_2$ nanoparticles, and/or a coating liquid containing these. Inventive materials may use no more than 5, 4, 3, 2.5, 2, 1, 0.5, 0.1, 0.01, 0.001, 0.0001, or 0.00001 wt. %, relative to total nanoparticle weight, of radical initiators, such as azobisisobutyronitrile, individually or in combination. The silver and/or titania nanoparticles need not be covalently bonded to the polymer matrix, and/or need not be copolymerized with the monomers of the polymer matrix.

Inventive materials may avoid the use of zinc oxide(s), such as $ZnO_2$, or may use no more than 5, 4.5 4, 3.5, 3, 2.5, 2, 1.5, 1, 0.5, 0.1, 0.01, 0.001, 0.0001, or 0.00001 wt. %, relative to total nanoparticle weight, of such zinc oxide(s). Inventive materials may avoid the use of non-polyethylene polymers, such as acrylics (PMMA, PAA, etc.), PVC, PU, polypropylene random copolymer, PP, ethylene-vinyl acetate copolymer, and/or ABS copolymer, or the polymer matrix may contain no more than 5, 4.5 4, 3.5, 3, 2.5, 2, 1.5, 1, 0.5, 0.1, 0.01, 0.001, 0.0001, or 0.00001 wt. %, relative to total polymer weight, of such non-PE polymers, individually or in combination. Inventive materials may avoid amine resins, or may contain no more than 5, 4.5 4, 3.5, 3, 2.5, 2, 1.5, 1, 0.5, 0.1, 0.01, 0.001, 0.0001, or 0.00001 wt. %, relative to total polymer weight, of such amine resins. Inventive materials may avoid polysaccharides, such as cellulose, starch, chitin, chitosan, pectine, and agar, or contain no more than 5, 4, 3, 2.5, 2, 1, 0.5, 0.1, 0.01, 0.001, 0.0001, or 0.00001 wt. %, relative to total polymer weight, of such polysaccharides, individually or in combination.

Inventive materials may avoid certain minerals, such as montmorillonite, wollastonite, sepiolite, chlorite, muscovite, illite, cookeite, bentonite, serpentine(s), antigorite, chrysotile, lizardite, clay(s), halloysite, kaolinite, vermiculite, talc, palygorskite, pyrophyllite, mica(s), biotite, fuchsite, phlogopite, lepidolite, margarite, glauconite, zeolite(s), natrolite, erionite, chabazite, heulandite, stilbite, scolecite, mordenite, analcime, scapolite(s), marialite, meionite, feldspathoid(s), nosean, cancrinite, leucite, nepheline, sodalite, hauyne, lazurite, feldspar(s), microcline, orthoclase, anorthoclase, sanidine, plagioclase feldspars, albite, oligoclase, andesine, labradorite, bytownite, anorthite, quartz(es), quartz, tridymite, cristobalite, coesite, stishovite, moganite, and/or chalcedony, or contain no more than 5, 4, 3, 2.5, 2, 1, 0.5, 0.1, 0.01, 0.001, 0.0001, or 0.00001 wt. % of such minerals, relative to total composition weight or total inorganic weight, individually or in combination. Inventive materials may avoid fillers, such as calcium titanate, calcium oxide, calcium sulfate, and/or calcium sulfite, or contain no more than 5, 4, 3, 2.5, 2, 1, 0.5, 0.1, 0.01, 0.001, 0.0001, or 0.00001 wt. % of such fillers, relative to total inorganic weight, individually or in combination. Inventive formulations require no wax compatibilizers or other wax components, such as PE wax and/or paraffin wax, or may use no more than 5, 4, 3, 2.5, 2, 1, 0.5, 0.1, 0.01, 0.001, 0.0001, or 0.00001 wt. %, relative to total polymer matrix weight, of wax(es), either alone or in combination.

Inventive materials can avoid surface modification of the silver and/or titania nanoparticles, such as using silane surface modifiers, including vinyltriethoxysiloxane, trimethyl silyl chloride, N-(β-aminoethyl)-γ-aminopropyltrimethoxysilane, N-2-aminoethyl-3-aminopropylmethyl dimethoxysilane, etc., or may use no more than 5, 4, 3, 2.5, 2, 1, 0.5, 0.1, 0.01, 0.001, 0.0001, or 0.00001 wt. %, relative to total nanoparticle weight, of surface modifying agents, such as silane surface modifiers. Inventive materials may avoid acrylate monomers and/or fluorinated monomers, such as hexafluorobutyl acrylate and/or methacrylate, or may use no more than 5, 4, 3, 2.5, 2, 1, 0.5, 0.1, 0.01, 0.001, 0.0001, or 0.00001 wt. %, relative to total monomer weight, of such acrylate monomers and/or fluorinated monomers.

The polymer matrix may include a polyolefn (such as polyethylene (PE), e.g., low density polyethylene, linear low density polyethylene, medium density polyethylene, high density polyethylene, polypropylene (PP), polybutylene (PB-1), polyisobutene (PIB), etc.), polyamide (such as nylon 6, nylon 11, nylon 12, nylon 6,6, nylon 5,10, nylon 1,6, aramid, etc.), polyimide, polyester (such as polyethyl terephthalate (PET), polybutyl terephthalate (PBT), polyethylene naphthalate (PEN), polytrimethylene terephthalate (PTT), polyhydroxybutyrate (PHB), polycaprolactone (PCL), polylactic acid (PLA), polyglycolide/polyglycolic acid (PGA), polyhydroxyalkanoate (PHA), polyethylene adipate (PEA), polybutylene succinate (PBS), poly(3-hydroxybutyrate-co-3-hydroxyvalerate) (PHBV), etc.), polyether (such as paraformaldehyde, polyethylene glycol (PEG), polypropylene glycol (PPG), polytetramethylene glycol (PTMG), etc.), vinylic (such as polyvinylalcohol (PVA), polyvinyl chloride (PVC), polyvinyl acetate, etc.), polycarbonate, polysulfone, and/or polyurethane, or two or more of any of these (e.g., two PUs, a PU and a polyester, two polyamides and a polyether, etc.). Particularly useful in several applications are polyethylene polymers, such as ultra-high-molecular-weight polyethylene (UHMWPE), high-density polyethylene (HDPE), cross-linked polyethylene (PEX or XLPE), medium-density polyethylene (MDPE), linear low-density polyethylene (LLDPE), low-density polyethylene (LDPE), very-low-density polyethylene (VLDPE), and the like.

Aspects of the invention provide increasing the antibacterial activity of combined silver-titanium oxide surface nanoparticles, e.g., 4, 5, 6, 7, 8, 10, 12.5, 15, 20, 25-fold or more that of $TiO_2$ alone.

Aspects of the invention comprise reducing or preventing the spread of bacteria, which may be Gram-positive, Gram-negative, multi-drug resistant or otherwise. Such bacteria may include *Bacillus, Pseudomonas, Staphylococcus*, and/or *Micrococcus*, such as *Virgibacillus, Lactobacillus reuteri, Lactobacillus acidophilus, E. coli, Bacillus anthracis, Bifidobacterium animalis, Bacillus subtilis*, etc.) (*Helicobacter pylori*, enteritis *Salmonella, Streptococcus thermophilus, Streptococcus pyogenes, Salmonella typhi, Mycobacteria, Clostridium tetani, Yersinia pestis, M. luteus, M. roseus*, and/or *M. varians*, e.g., *acinetobacter* spp., *alcaligenes* spp., *bacillus* spp., *bordetella* spp., *campylobacter* spp., *citrobacter* spp., *clostridium* spp., *corynebacterium* spp., *escherichia* spp., *enterobacter* spp., *enterococcus* spp., *flavobacterium* spp., *klebsiella* spp., *legionella* spp, *listeria* spp., *micrococcus* spp., *mycobacterium* spp., *nocardia* spp., *proteus* spp., *providencia* spp., *pseudomonas* spp., *salmonella* spp., *serratia* spp., *shigella* spp., *staphylococcus* spp., *streptococcus* spp., *streptomyces* spp., *thermomonospora* spp., *yersinia* spp., etc. Other relevant bacterium classes may include acidobacteria, actinobacteria, aquificae, armatimonadetes, bacteroidetes, caldiserica, chlamydiae, chlorobi, chloroflexi, chrysiogenetes, coprothermobacterota, cyanobacteria, deferribacteres, deinococcus-thermus, dictyoglomi, elusimicrobia, fibrobacteres, firmicutes, fusobacteria, gemmatimonadetes, lentisphaerae, nitrospirae, planctomycetes, proteobacteria, spirochaetes, synergistetes, tenericutes, thermodesulfobacteria, thermotogae, and/or verrucomicrobia. In addition or alternatively, inventive films and/or devices may reduce or prevent mycosis, i.e., fungal infection (s), including Candidiasis, Cryptococcosis, Aspergillosis, Tinea versicolor infection, dermatophytosis, or combinations of these. Inventive films and/or devices may reduce or prevent one or more superficial mycosis, cutaneous mycosis, subcutaneous mycosis, primary pathogen mycosis, and/or opportunistic pathogen mycosis.

EXAMPLES

The degree of photocatalytic activity of $TiO_2$ is generally influenced or governed by the size and extent of the particles dispersion state when added to polymer matrices. Different concentrations by weight, such as 1, 3, 5, and 7 wt. % of $TiO_2$ and 3.0 wt. % of $AgNO_3$ were added to an FDA approved, biomedical quality polyethylene material (40 wt. % in methanol) which was subjected to methanol treatment for 1 hour prior to the addition.

The synthesis of $TiO_2$—Ag-nanocomposites was carried out via different synthetic techniques. The particles can be made in the manner described in, for example, Shahab Ansari Amin et al., Powder Technology 196 (2009) 241-245—incorporated herein by reference in its entirety).

An example of a chemical modification using chemically-modified Ag/$TiO_2$ nanocoated (LDPE) is described below. The Ag/$TiO_2$-nanocomposite powder was synthesized by a chemical method using a reducing agent and then chemical coating of LDPE with the Ag/$TiO_2$. First LDPE was treated with methanol for 1 hr before being nanocoated with Ag nanoparticles after reduction reaction between $AgNO_3$ (silver-nitrate) and $NaBH_4$ (sodium borohydride). The $AgNO_3$ (30 wt. %) solution was also added drop-wise to a $TiO_2$ colloidal solution (1,3,5,7, wt. %) in a dark container, while being vigorously stirred at room temperature. The suspension was stirred for 30 min. The final Ag/$TiO_2$ sol was orange-brown and semi-transparent.

Different concentrations by weight as 1, 3, 5, 7 wt. % of $TiO_2$ and $AgNO_3$ as 3.0 wt. % were added to the polyethylene (40 wt. %) which was primarily subjected to methanol for 1 hour. Chemical coating was conducting by melt mixing process for 1 hour at 104° C. to create Ag/$TiO_2$ LDPE nanocomposite film.

Using low density polyethylene as primary polymer with titanium oxide nanoparticles ($TiO_2$ nanoparticles) in presence of $AgNO_3$ as a source of Ag nanoparticles after reduction with 0.5 mol/mL sodium borohydride can provide a nanocomposite that is antimicrobial effective against many of gram positive and gram-negative bacterial infections during the use of virtual reality equipment in the treatment of pain in healthcare patients in various clinical settings.

The surface morphology of the Ag/$TiO_2$ LDPE nanocomposite film was analyzed by a scanning electron microscope. The Ag weight percentage in the Ag/$TiO_2$ LDPE films were calculated to be 1 to 5 wt. % wt %, corresponding to the molar ratio of Ag to $TiO_2$. In the SEM, the surface morphology of the varying sizes of 50-100 nm Ag/$TiO_2$ LDPE nanocomposite films. It was found that Ag nanoparticles were dispersed uniformly in the $TiO_2$ layer without aggregation. Interestingly, Ag nanoparticles exhibited the form of round crystal nanoparticles (the diameter was between 30-50 nm), which were clearly seen in SEM at the lower ratios of Ag (i.e., 1.0 w %). At the higher ratio of Ag (5.0 wt. %) the nanoparticles were dominated by the round crystal growth, nano round morphology; where at higher Ag concentration (e.g., 5 mol %), the nanoparticles possessed the nanocrystal growth. In some embodiment the nanoparticles are well distributed in the polymer matrix, although a slight agglomeration in the nanocomposite containing 2 wt %. of $TiO_2$ nanoparticles is observed.

An exemplary useful polyethylene polymer in the Examples can be obtained commercially from SABIC, having the following exemplary property values: (i) a density of 919 kg/$m^3$ according to ASTM D1505; (ii) a dry flow of 23 seconds ISO 6186; (iii) an average particle size powder of less than 600 μm according to ASTM D1921; and (iv) a melting point of 104° C. according to DIN 53765.

Aspects of the invention include nanocomposite protective glove or films for a cover for virtual reality instruments comprising polyethylene with silver (Ag) and titanium dioxide ($TiO_2$) nanoparticles. Aspects of the invention provide a melt mixing process conducted, for example, for around 1 hour, e.g., at least 30, 40, 45, 50, 55, 60, 65, 70, 75, 80, or 90 minutes and/or up to 3, 2.75, 2.5, 2.25, 2, 1.75, 1.5, 1.25, 1, or 0.75 hours, at 104° C. (or at the melting point or glass transition temperature of the polymer ±1, 2.5, 3.33, 5, 7.5, or 10%) to create nanocomposite covers, optionally having good elasticity and/or viscosity, and/or optionally having antimicrobial (e.g., bacterial and/or fungal) properties, which can be used safely as covers on hospital equipment, including virtual reality instrumentation, with antibacterial characteristics.

Although the antimicrobial properties of $TiO_2$ nanoparticles and their application in medicine have gained more attention in recent years, surprising combinatorial effects have been developed as an aspect of the present invention. Aspects of the invention may provide antimicrobial effects of titanium dioxide nanoparticles on pathogenic strains of Gram-negative *Escherichia coli* and Gram-positive *Staphylococcus aureus*. Aspects of the invention may provide titanium dioxide nanoparticles, which alone or in combination with silver nanoparticles, can cause pores to form in bacterial cell walls, leading to increased permeability and cell death. Aspects of the invention comprise using titanium dioxide nanoparticles for efficient antibacterial effects or treatments and/or as an antibacterial agent for various coating and/or shielding purposes, particularly for covering medical and/or dental equipment or devices, preferably virtual reality instruments. Aspects of the invention include incorporating different percentages (wt. %) of silver and titanium dioxide nanoparticles to obtain a mixture with excellent antimicrobial properties. A polymer matrix, such as polyethylene, may be used as a host for one or more surface coatings with silver and titanium dioxide nanoparticles, which may protect against bacteria and fungi. Aspects of the invention include reactions of silver on the surface of titanium dioxide to improve the photocatalytic activity of the titanium dioxide.

Nanoparticle-coated polyethylene polymer including a mixture of silver and titanium dioxide nanoparticles can provide a protective cover for virtual reality devices with antibacterial properties to 1, 2, 3, 4, 5, 8, 10, 15, 20, 25, 35, 50, 75, 100, or more types of bacterial and/or fungal infections potentially arising from cross contamination conventionally risked using the same virtual reality equipment between patients in healthcare facilities.

Virtual reality presentation/projection has been implemented in hospitals and health care settings to provide a means of escape and distraction for certain patients, for example, those receiving chemotherapy treatment, patients with burns, patients in dental clinics, patients in physiotherapy clinics, etc. The risk of bacterial and/or fungal infection while using common virtual reality (or other hospital) equipment can still exist even after disinfection with conventional disinfectants, like alcohol or hydrogen peroxide, and the use of inventive covers can reduce this risk, e.g., 1, 2.5, 5, 7.5, 10, 15, 20, 25, 33, 40, 50%, or more. Patients may use the virtual reality equipment for minimum durations of 15, 20, 30, 45, 60, 90, 120, or more minutes, and cross contamination is especially problematic in isolated patients with multi-resistant bacteria species, which can be limited and/or avoided using inventive films/foils.

Nanocomposites of $TiO_2$ and Ag on and/or in polyethylene polymer with antibacterial and/or antifungal effects can provide protective covers for equipment generally, but particularly for virtual reality equipment, and can minimize the risk of infection. Aspects of the invention include reducing the waste of resources and/or high costs of procuring new equipment, padding, covers, antibacterial cleaners, and the like, while reducing the cross contamination of patients from equipment, especially in high-risk contamination cases.

Aspects of the invention allow the use of virtual reality equipment in pain management without requiring the use of decontamination fluids and/or without hosting vectors and/or limiting the spread of disease agents.

Aspects of the invention comprise Ag and $TiO_2$ nanocomposite-coated LDPE membrane. The $TiO_2$ may have a particle diameter of no more than 75, 60, 50, 40, 30, 25, 20, 17.5, 15, 12.5, 10, 7.5, 5, or 2.5 nm which increase the nanoscale matrix mixing with silver nanoparticles, and/or provide material properties with efficient dispersion and textured surfaces useful to inhibit bacteria adhesion and growth against both gram-negative and gram positive bacteria strains on contacted skin, e.g., by contacting such skin with chemically-modified and an $Ag/TiO_2$ nanocoated LDPE membrane. Aspects of the invention provide antimicrobial surfaces which inhibit or lessen the growth of microorganisms, e.g., by chemical modifications, using chemically-modified $Ag/TiO_2$ nanocoated (LDPE) membranes.

The crystalline forms of $TiO_2$ mainly include anatase and/or a $TiO_2$ that includes partially crystallized material with a high amount of material remaining amorphous after thermal treatment (e.g., 20-40% amorphous). Preferably the $TiO_2$ having a crystallization grade around 100%.

An agglomeration phenomenon occurring with small particle size results in a large specific surface area and the high surface energy of $Ag/TiO_2$ which preferably have smooth crystal planes. Relatively speaking, the fine particles of $Ag/TiO_2$ are more than that of pure $TiO_2$, which may be attributed to Ag deposition. It is indicated that the deposition of Ag on the surface of $TiO_2$ increases the crystallinity but decreases the grain size.

The morphology of high energy crystalline surface titanium dioxide and Ag nanoparticles is uniform and regular truncated octahedral morphology, and the particle size is mostly in the nanometer level (50-100 nm), thus making the specific surface area of Ag—$TiO_2$ larger. High energy crystal surface titanium dioxide and Ag nanoparticles may constitute large aggregate particles, each in the nanometer range (aggregates of 1-100, 10-50 μm) and significantly uniformly distributed on the coated LDPE films.

Incorporating Ag nanoparticles into $TiO_2$ on nanocoated LDPE films results in increasing surface area (surface area per mass, porosity), reducing particle size, generating structured mesoporous materials, creating a double-phase structure more than that of pure $TiO_2$ (e.g., 98.2 $m^2/g$).

The LDPE film was fully coated with $Ag/TiO_2$ nanoparticles forming a dense covering around the LDPE film. The $Ag/TiO_2$ nanoparticles used preferably have a narrow size distribution, and the density of particles per unit area for the LDPE was very high. The nanoparticles work as a cover (coating layer) around the LDPE.

Aspects of the invention chemically modify the particles by mixing LDPE or other suitable polymer material with methanol or other suitable solvent(s) before adding $TiO_2$ and Ag nanoparticles in melting processes, optionally involving thermal reduction during melting, to produce viable membrane materials with a brownish-grey color resistant to the development of micro-organisms. Aspects of the invention provide coatings and/or covers for medical, dental/orthodontal, and/or entertainment devices having superior effects on bacterial cell adhesion and/or development from Gram-positive and/or Gram-negative bacterial strains. Aspects of the invention provide improved antimicrobial activity via hydrophobicity of the coated membrane and/or surface roughness, which can be related. Aspects of the invention included changing bacterial adhesion mechanisms and/or abilities. Aspects of the invention may induce one or more changes in the morphological changes in the bacteria, e.g., using titania and silver nanoparticles on a film, such as LDPE.

The nanocoated (nanocomposite) $Ag/TiO_2$ LDPE materials were characterized regarding their morphology, composition, nanoparticle dispersion, tensile properties, crystallinity, conductivity, thermal properties, photocatalytic, and antibacterial activity.

The LDPE nanocomposite films have antibacterial properties against different Gram negative and Gram-positive bacteria (e.g. *Pseudomonas* and *Enterococcus*), e.g., an up to 5- and 8-log reduction.

Mechanical characteristics were investigated by tensile strength (am) of 40% LDPE. The tensile strength (Mpa) 11.421 increased to 18.378 after coating with $Ag/TiO_2$ nanoparticles. However, with respect to the LDPE $Ag/TiO_2$ nanocomposites film, tensile strength increased with the increase in nano $Ag/TiO_2$ concentration (wt %). The $Ag/TiO_2$ nanoparticle of $TiO_2$ may reinforce the matrix thereby contributing to an increase in tensile strength of the nanocomposites.

It was observed that the significant improvement of mechanical properties, electrical and thermal conductivity in LDPE nanocomposites film was dependent on the Ag/$TiO_2$ concentration (wt %) and resulting roughness, agglomeration, and large surface area created on the nano LDPE film and also their compositions. However, increase of tensile strength due to high surface area of Ag/$TiO_2$ which lead to interactions with LDPE film in nano scale matrix.

Aspects of the invention provide well-dispersed nanoparticles in and/or on the polymer matrix, whereby inventive composite membranes made with 3 wt. % silver nitrate may have improved crystallinity. Inventive nanocomposite filaments may display both antibacterial and photocatalytic activity, thereby offering potential applications in medical and/or entertainment devices, optionally via improved inhibition of bacterial cell adhesion. Aspects of the invention provide good dispersion of $TiO_2$ and Ag nanoparticles in the polymer matrix, particularly LDPE membranes, thereby leading to the higher tensile strength. Aspects of the invention may provide nanocomposite $TiO_2$ and Ag nanoparticles in an LDPE membrane with a thickness of 25±1, 2, 3, 4, or 5 μm, e.g., at least 25, 30, 35, 40, 50, 60, or 75 μm and/or no more than 500, 450, 400, 350, 300, 250, 200, 175, 150, 125, 100, or 75 am, optionally comprising an adhesive layer of the nanocomposite for attachment of the membrane (film) to other portions of the medical device.

Without wishing to be bound to theory, the nanocomposites coated on the LDPE membrane have a potent antimicrobial effect when attached to the membrane presumably due to the excellent physicochemical and biological properties of silver nanoparticles (AgNPs) and due to photocatalytic properties of $TiO_2$ nanoparticles. Silver nanoparticles may fill the interspaces of matrix and hinder the transfer of 02 molecules through the film. The low hydrophilicity of $TiO_2$ may prevent the penetration of moisture into the LDPE membrane or film. Aspects of the invention may provide a barrier effect from $TiO_2$ particles, leading to a reduction in water vapor permeability and hence an increase in the adhesive properties of the created nanocomposites to the medical or entertainment device as antimicrobial tools.

Aspects of the invention include different concentrations by weight, e.g., 1, 3, 5, or 7 wt. % of $TiO_2$, e.g., at least 1, 1.5, 2, 2.5, 3, 3.5, 4, 4.5, or 5 wt. % and/or up to 10, 9.5, 9, 8.5, 8, 7.5, 7, 6.5, or 6 wt. %, and 3.0 wt. % $AgNO_3$, e.g., at least 1, 1.25, 1.5, 1.75, 2, 2.25, 2.5, 2.75, or 3 wt. % Ag and/or up to 5, 4.5, 4, 3.75, 3.5, 3.25, 3, 2.75, 2.5, 2.25, 2, or 1.75 wt. %, were added to a polymer, e.g., polyethylene, at 40 wt. %.

The nanocomposite membrane compositions preferably contain LDPE in an amount of 40 wt. % based on the total weight of the membrane. The LDPE is preferably a purified polymer with additive ingredients exhibiting a very flexible and tough form with a higher degree of short and long side-chain branching. Branching reduces the tendency of the molecules to pack closely together in hard, stiff, crystalline domains which results in lower density and crystallinity as well as in greater flexibility and toughness. However, LDPE has a significantly lower tensile strength, heat deflection temperature and melting point. It has smaller crystallites due to longer side and subside branching. The degree of crystallinity is usually in the range of 40% depending on branching and thermal history.

Low density (LDPE) and high density polyethylene (HDPE) were selected as doping phases since they are non-toxic and low cost polymers, with good chemical and thermal stability. A preferred polyethylene polymer has the following property values:

1. 0.91-0.93 g/$cm^3$
2. Softening point 94° C.
3. Dry flow 23 sec (ISO 6186)
4. Particle size powder<600 μm (ASTM D1921)
5. melting point 104° C. (DIN 53765)
6. MFI-melt flow index 1.44 g/10 min
7. Modulus of elasticity 240 MPa
8. Thermal conductivity 0.35 W/mK
9. Volume Resistivity 6×1015 Ohm-cm Such arrangements may provide sufficiently higher concentrations of nanoparticles to give sufficient plasticity and reduced elasticity, e.g., of LDPE, which in turn can lead to increased intermolecular attraction force, making the polymer (e.g., LDPE) membrane structure matrix dense and less permeable and increasing the antimicrobial effect of the nanocoated polymer (e.g., LDPE) membrane.

The addition of $TiO_2$ and Ag nanoparticles to LDPE pellets treated first with methanol can affect their mechanical properties. The mechanical characteristics of LDPE were investigated by measuring the tensile strength of the film (e.g., ASTM D882-18). Addition of nanocomposite coating of Ag/$TiO_2$ onto the polymer leads to better mechanical properties. In one embodiment the Ag/$TiO_2$ nanocomposites are present only on and/or partially embedded in the LDPE membrane and are not dispersed uniformly therein. LDPE is the preferred polymer and provides good flexibility, transparency, low-cost, easy processability, and thermal stability. The relationship within the polymer matrix characteristics (degree of crystallinity, visible light response, polarity) and radical-ions species were significantly affected with a nanocomposite coating of Ag/$TiO_2$ which in turn end by microbes' activations.

This may be because nanoparticles have a very large specific surface area that can affect interfacial strength and degree of dispersion, ostensibly leading to better inhibition of bacterial cell adhesion, in one or both of Gram-positive and Gram-negative bacterial strains, through hydrophobicity of the coated membrane. The reduced adhesion may derive from the surface roughness. The Ag/$TiO_2$ particles have surface area of 41.2 $m^2$/g and the particle surface area is proportional to the particle mass concentration. The most important increase was obtained for LDPE containing Ag/$TiO_2$ when functioning to affect tensile strength of the LDPE Ag/$TiO_2$ nanocomposite film, perhaps due to better dispersion in composite matrix, indicating that Ag/$TiO_2$ nanoparticles reinforce the matrix thereby contributing to an increase in tensile strength of the nanocomposites (see for example the SEM images).

The surface roughness parameters of LDPE nanocomposites coated Ag/$TiO_2$ film surfaces were obtained by scanning a surface area of 4 $\mu m^2$. Surface LDPE nanocomposites coated Ag/$TiO_2$ film display a bactericidal effect which may be attributed to mechanical stress exerted on the membrane of bacteria adhered to the LDPE nanocomposites coated Ag/$TiO_2$ film resulting in bacterial membrane stretching, rupture and death.

Figure 2A:
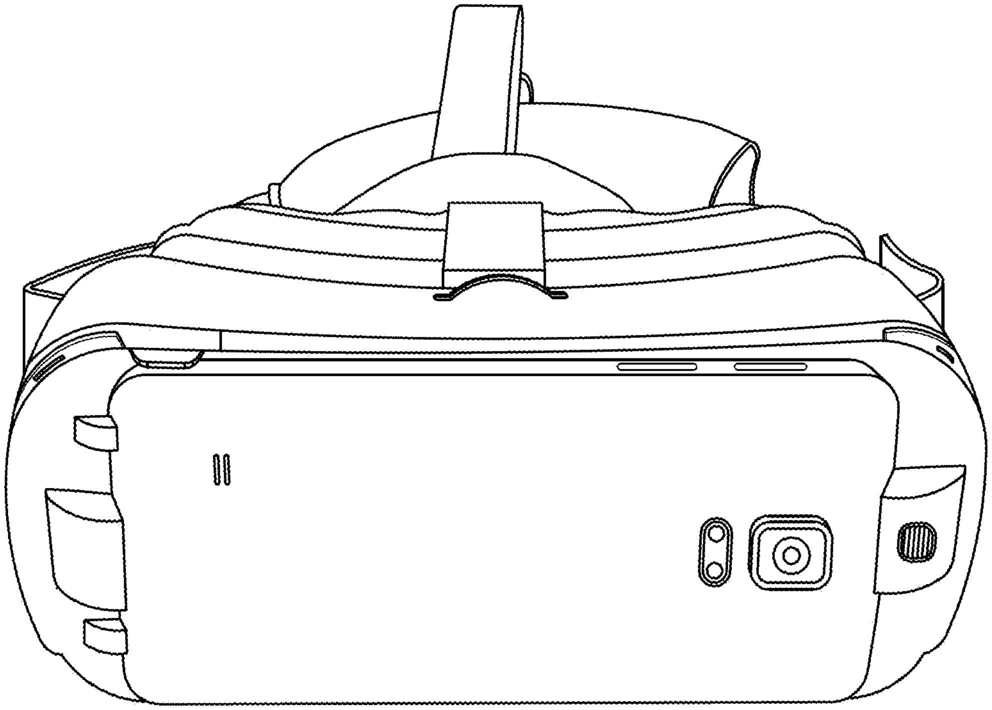
FIG. 2A to 2C show virtual reality (VR) goggles (2A and 2B) and a typical VR goggle cloth case (2C)
Figure 2B:
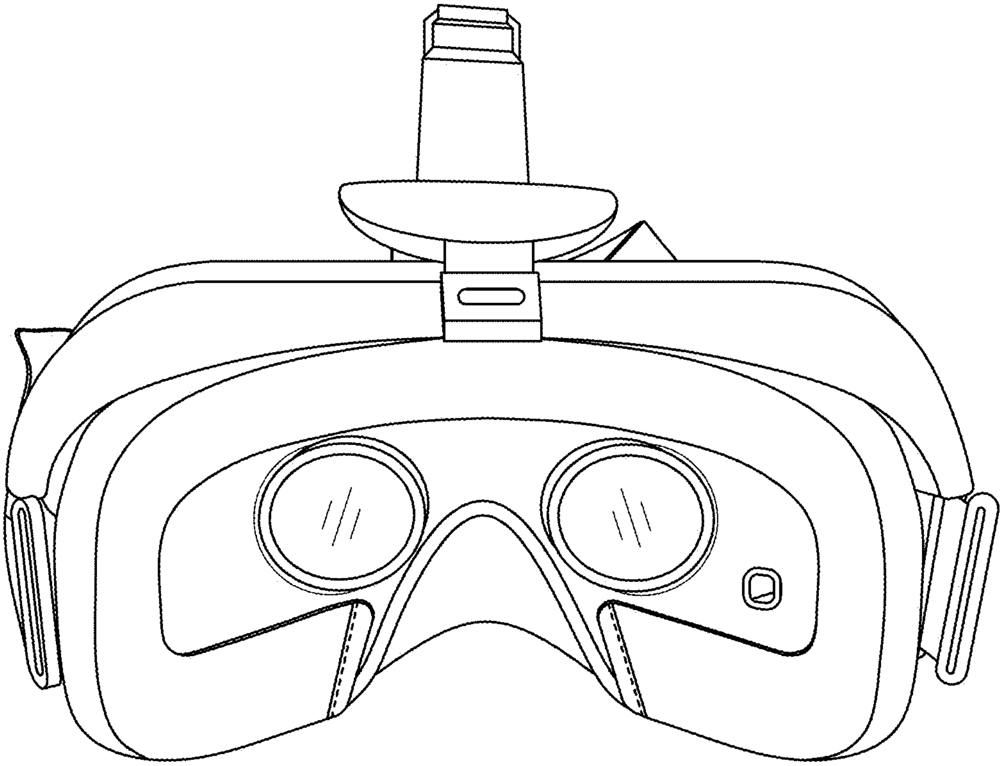
Figure 2C:
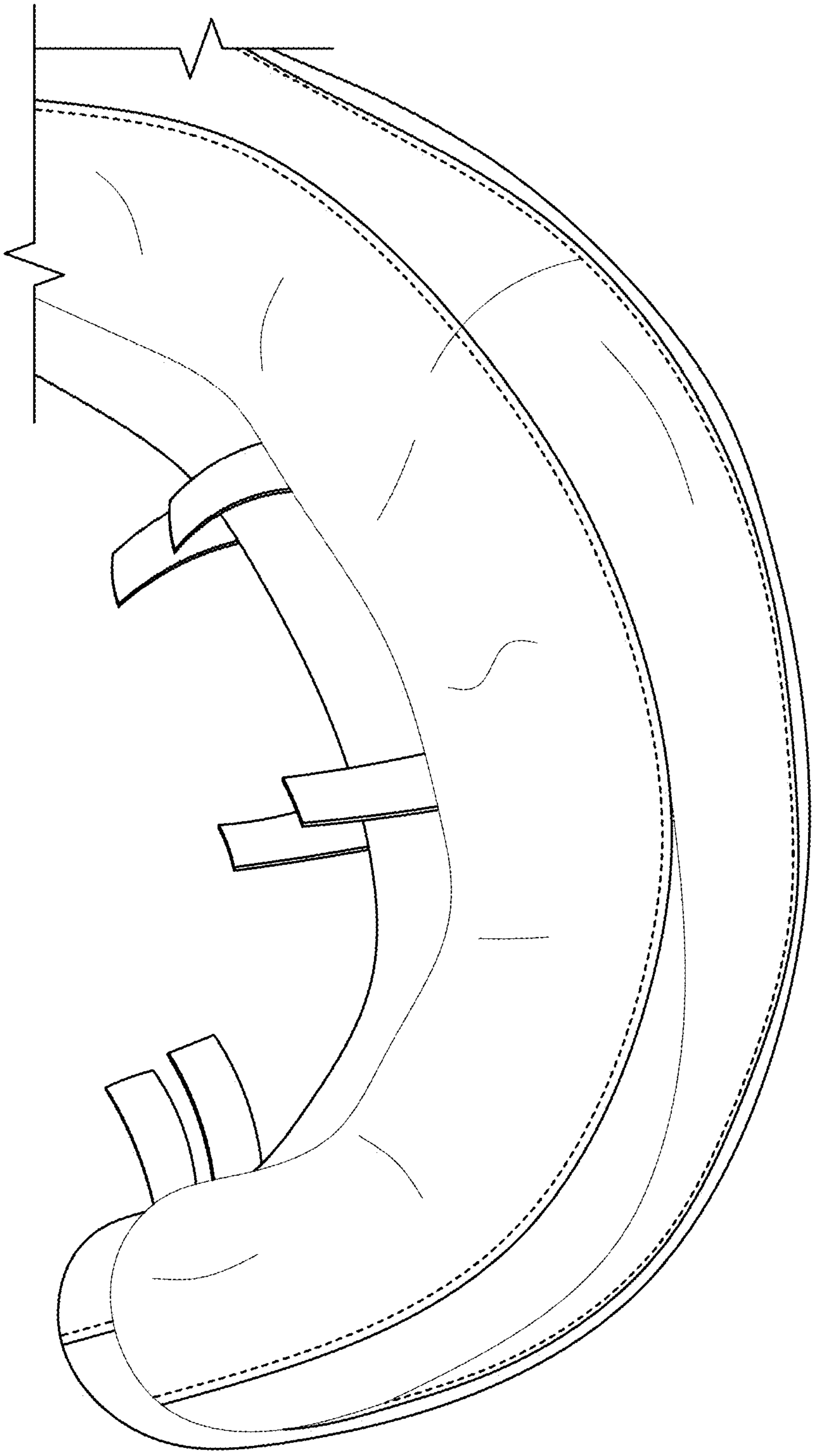
Figure 3A:
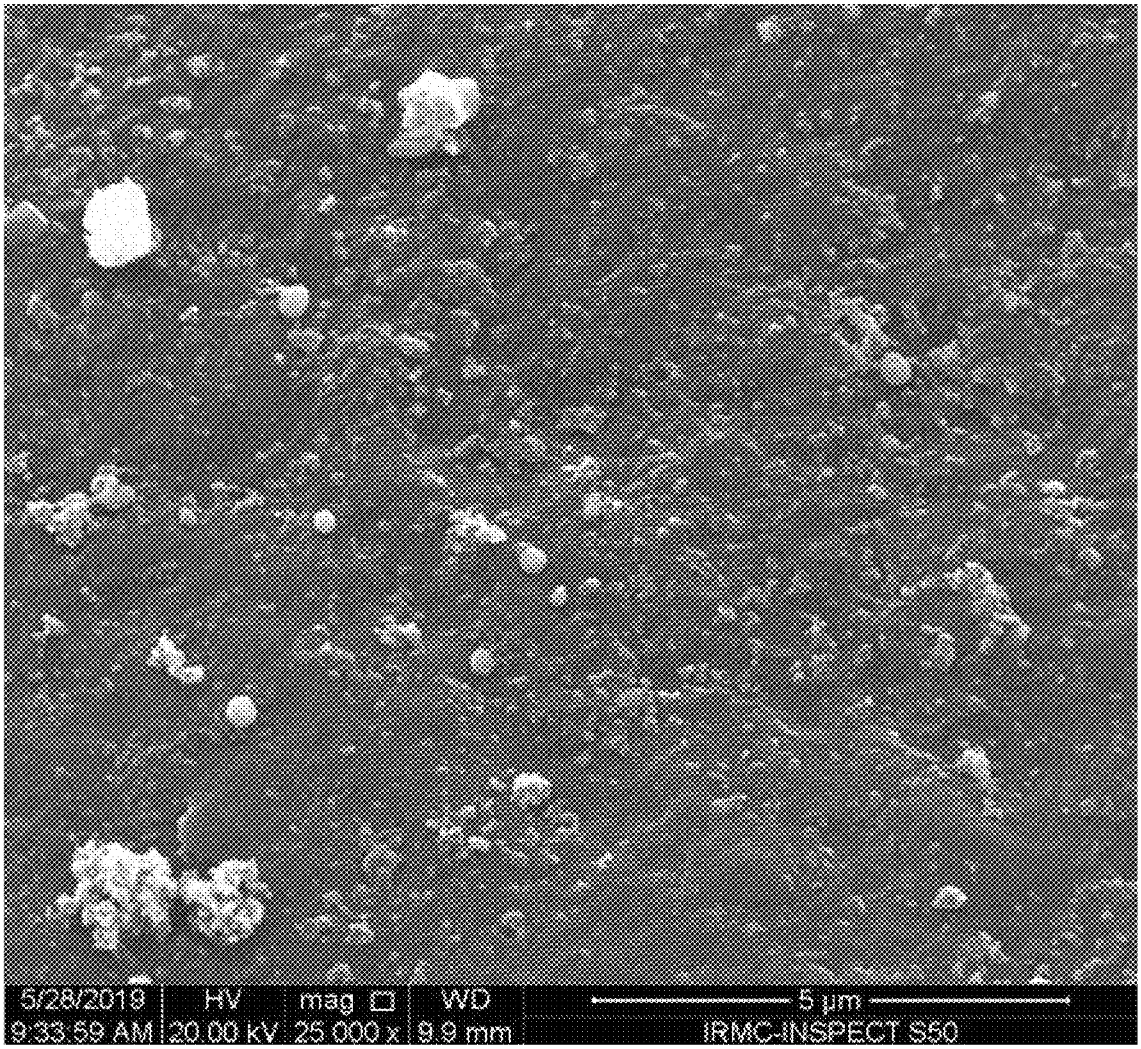
FIG. 3A to 3J show scanning electron microscope (SEM) images for exemplary nanocomposite polyethylene films coated with $TiO_2$ and Ag nanoparticles illustrating exemplary distributions on $TiO_2$ and Ag nanoparticles on large surface area on polyethylene on 5, 10, and 30 μm scale.
Figure 3B:
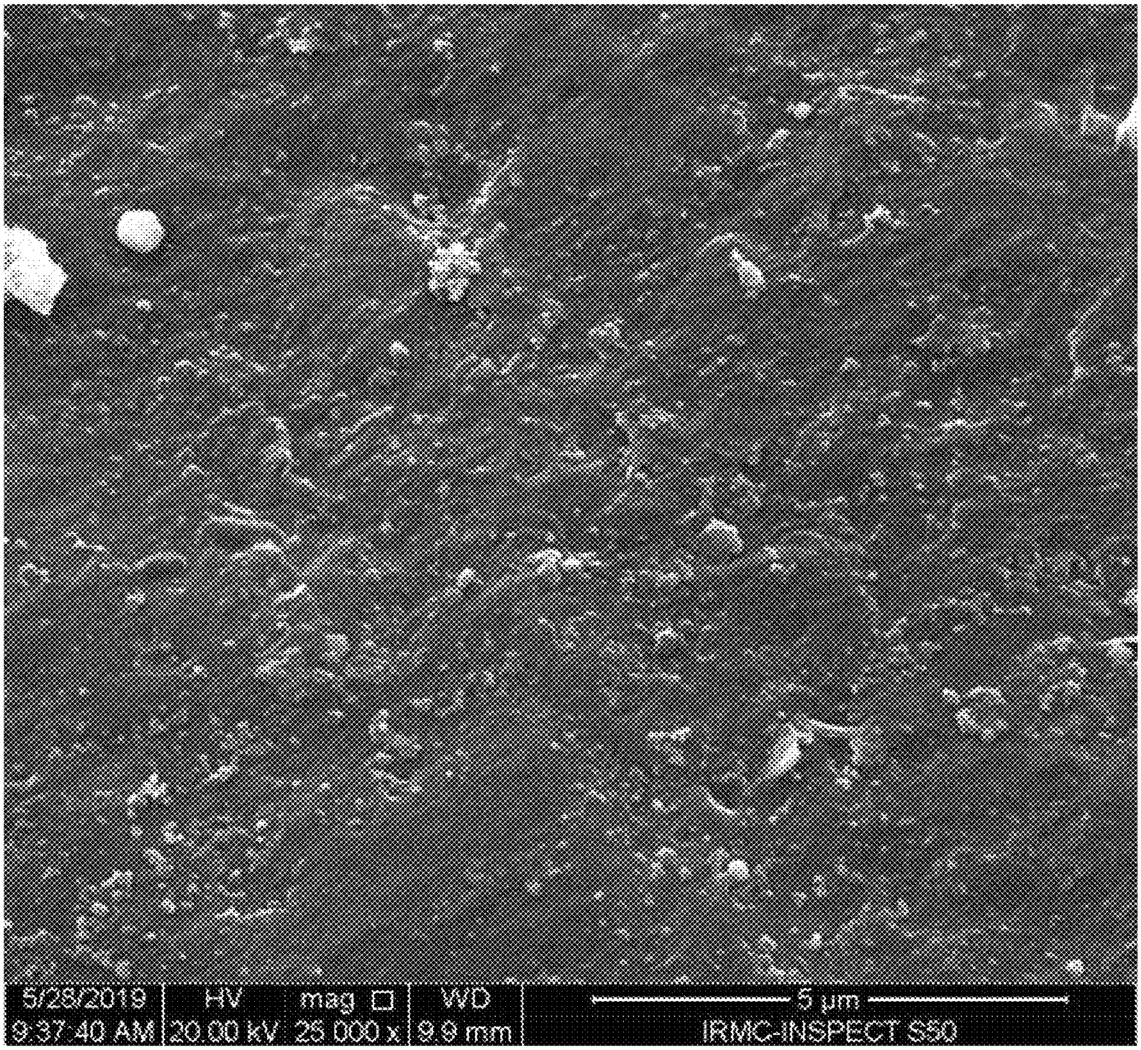
Figure 3C:
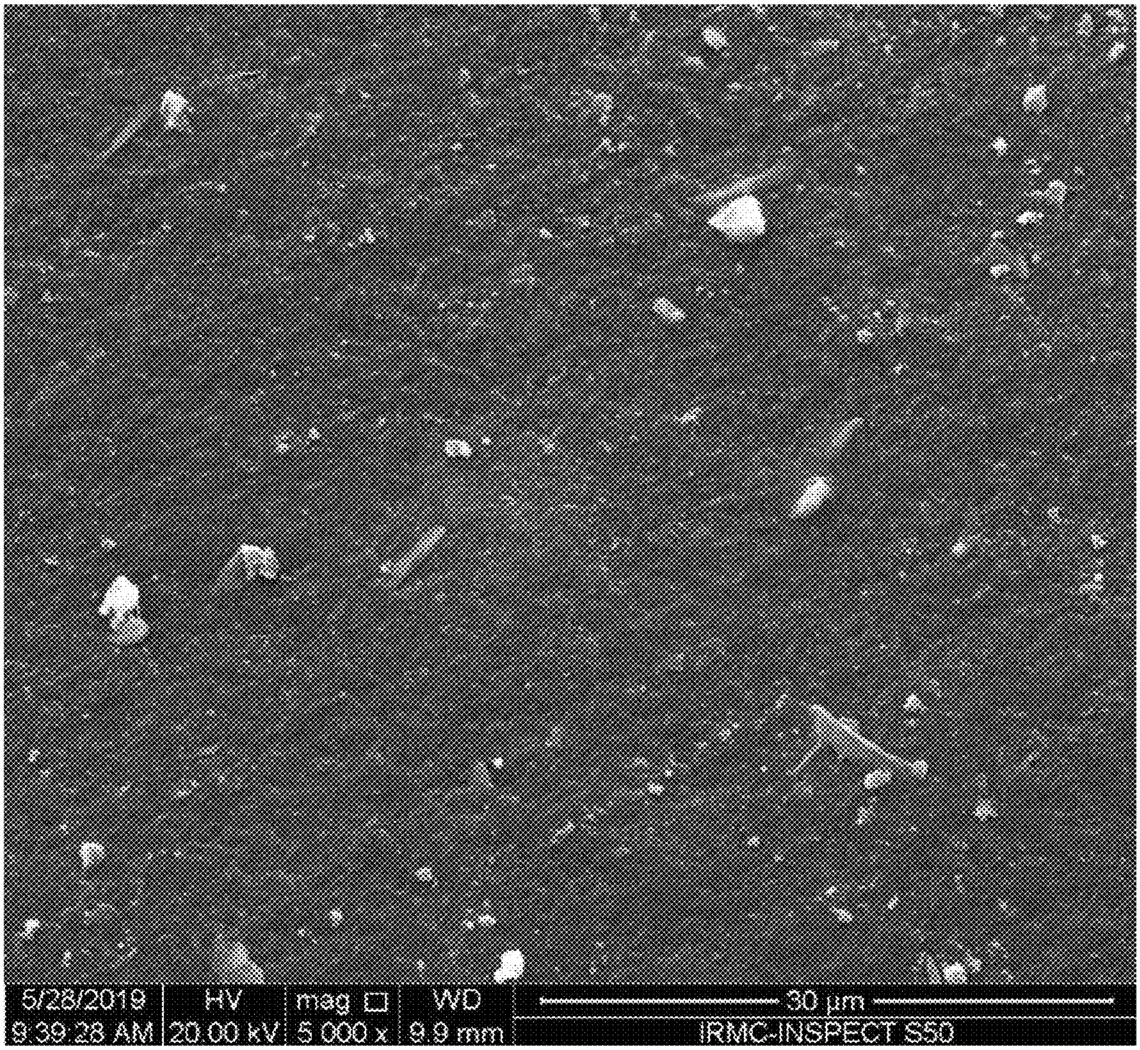
Figure 3D:
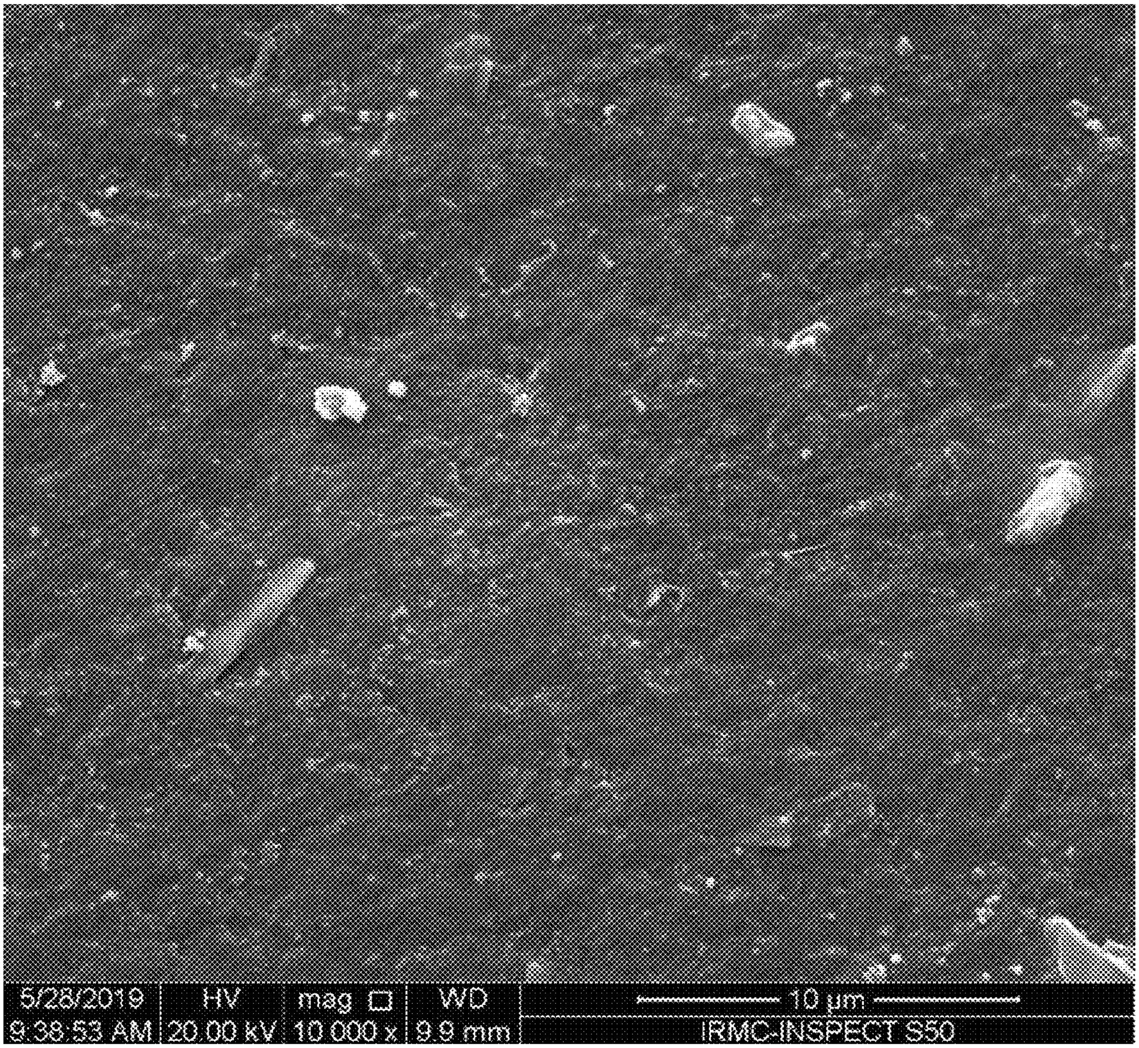
Figure 3E:
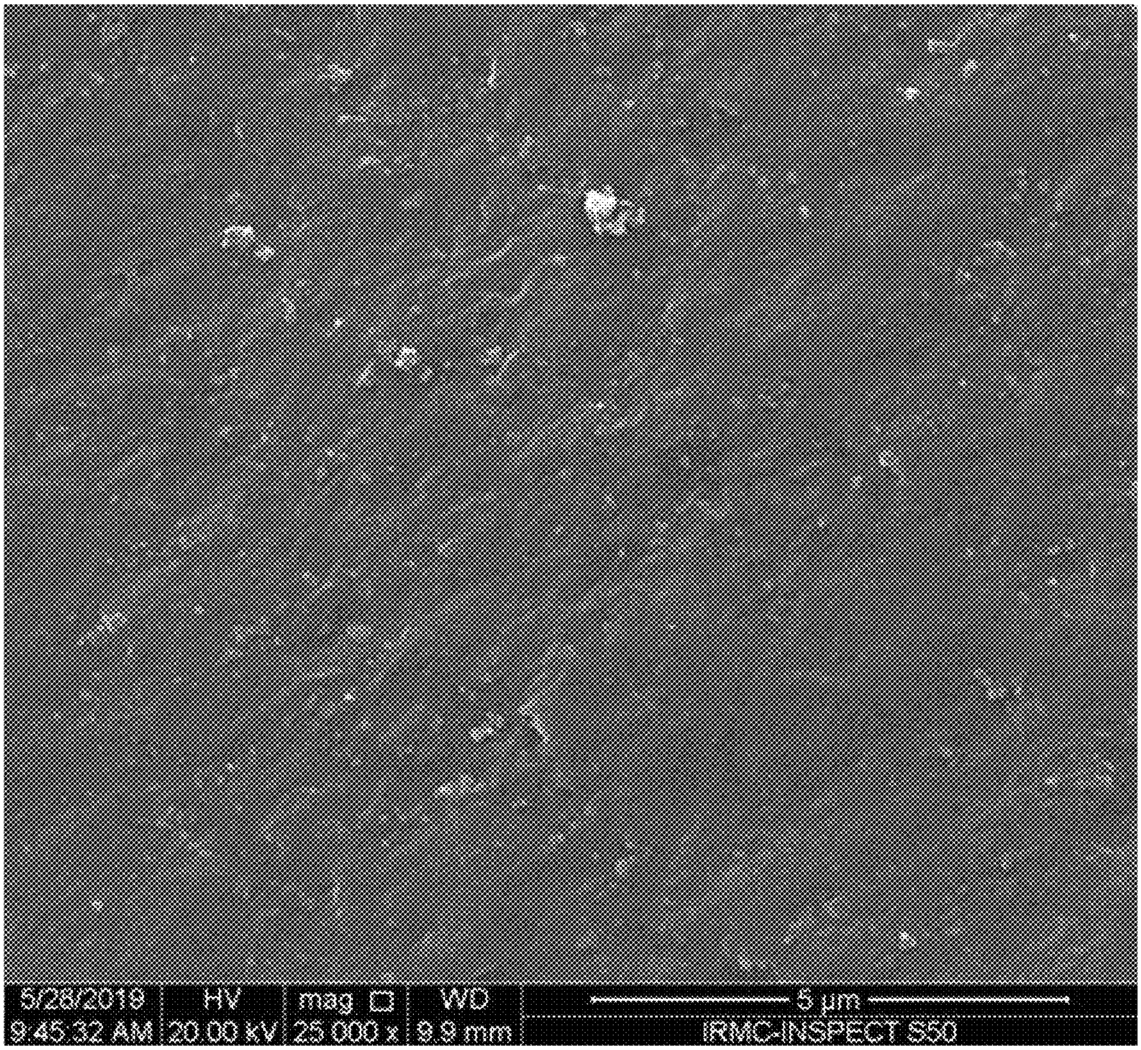
Figure 3F:
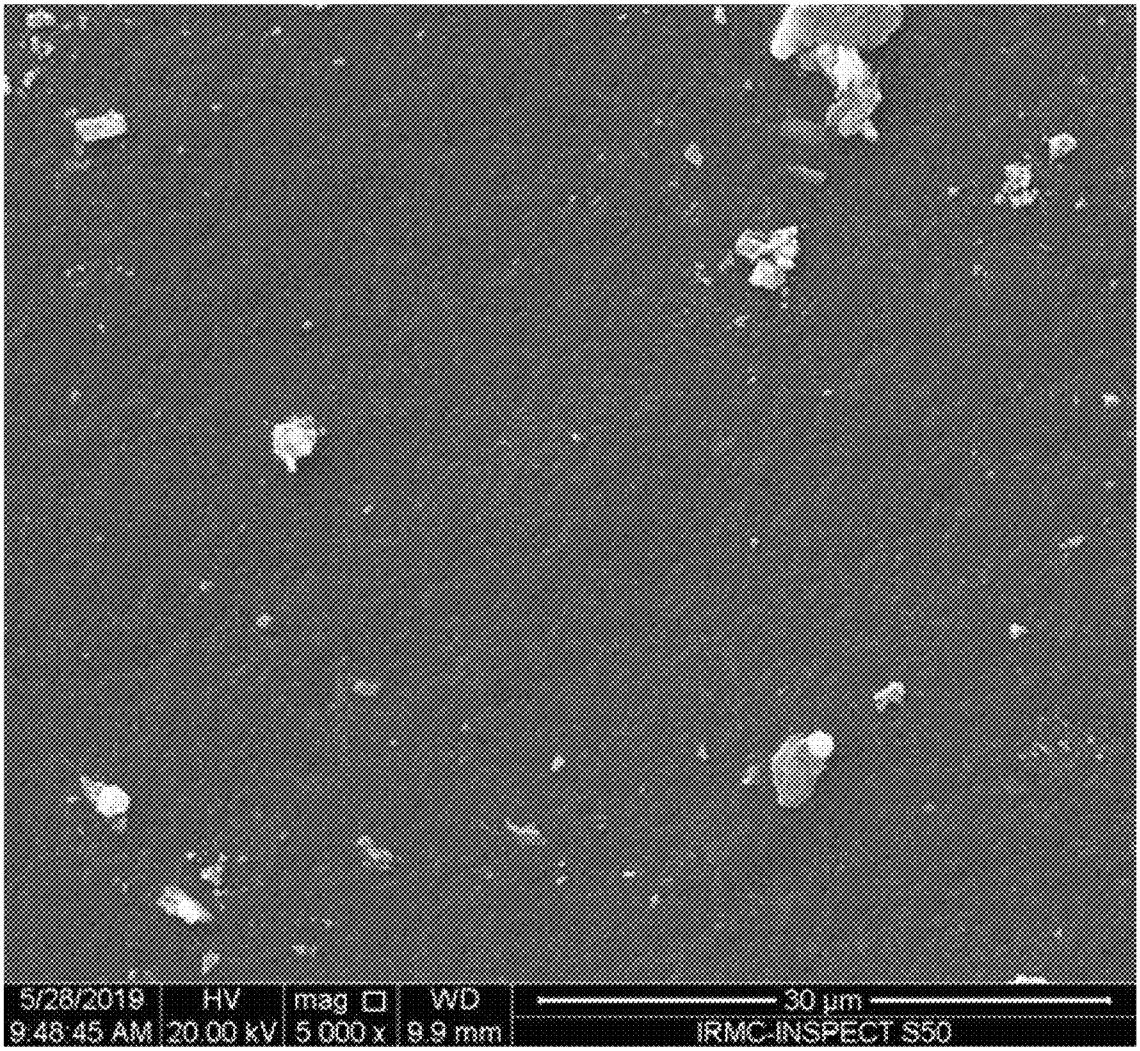

Aspects of the invention comprise changing the bacterial adhesion mechanism, optionally via surface roughness, as shown in SEM images FIG. 2A to 2J, particularly with the highest exemplary $TiO_2$ concentrations, and no growth of the invented membrane in the bacteriological test as shown in bacterial test plate in FIGS. 3A and 3B. For LDPE nanocomposites coated Ag/$TiO_2$ film, the particles are well dispersed in polymer matrix as shown SEM with a slight agglomeration. The average size of Ag/$TiO_2$ in the film are within 50-100 nm and mostly irregular in shape.

Referring now to the drawings, wherein like reference numerals designate identical or corresponding parts throughout the several views.

FIG. 1 shows a schematic representation of an exemplary preparative approach to obtain inventive materials. The upper reaction scheme depicts the suspension of polyethylene pellets, e.g., at a concentration of roughly 40 wt. %, in methanol. After one hour of swelling in the upper center of FIG. 1, methanol-swollen polyethylene particles are obtained, which are subsequently mixed with the product of the lower reaction scheme in FIG. 1. In the lower reaction scheme in FIG. 1, silver nitrate (3 wt. %), $Ag(NO_3)$, and sodium borohydride, $NaBH_4$ (0.5 mol/mL) are added and reacted, then mixed with $TiO_2$ and the methanol-swollen polyethylene particles. The mixed silver, titania, and methanol-swollen polyethylene particles are then at least partially melted on the right portion of FIG. 1, e.g., at a temperature of 104 C. for 1 hour, to obtain a polyethylene material containing silver and titania nanoparticles, generally as a coating comprising Ag and $TiO_2$.

FIG. 2A to 2C show virtual reality (VR) goggles (2A and 2B) and a typical VR goggle cloth case (2C) which are examples of devices with which the protective films may be used.

Figure 3G:
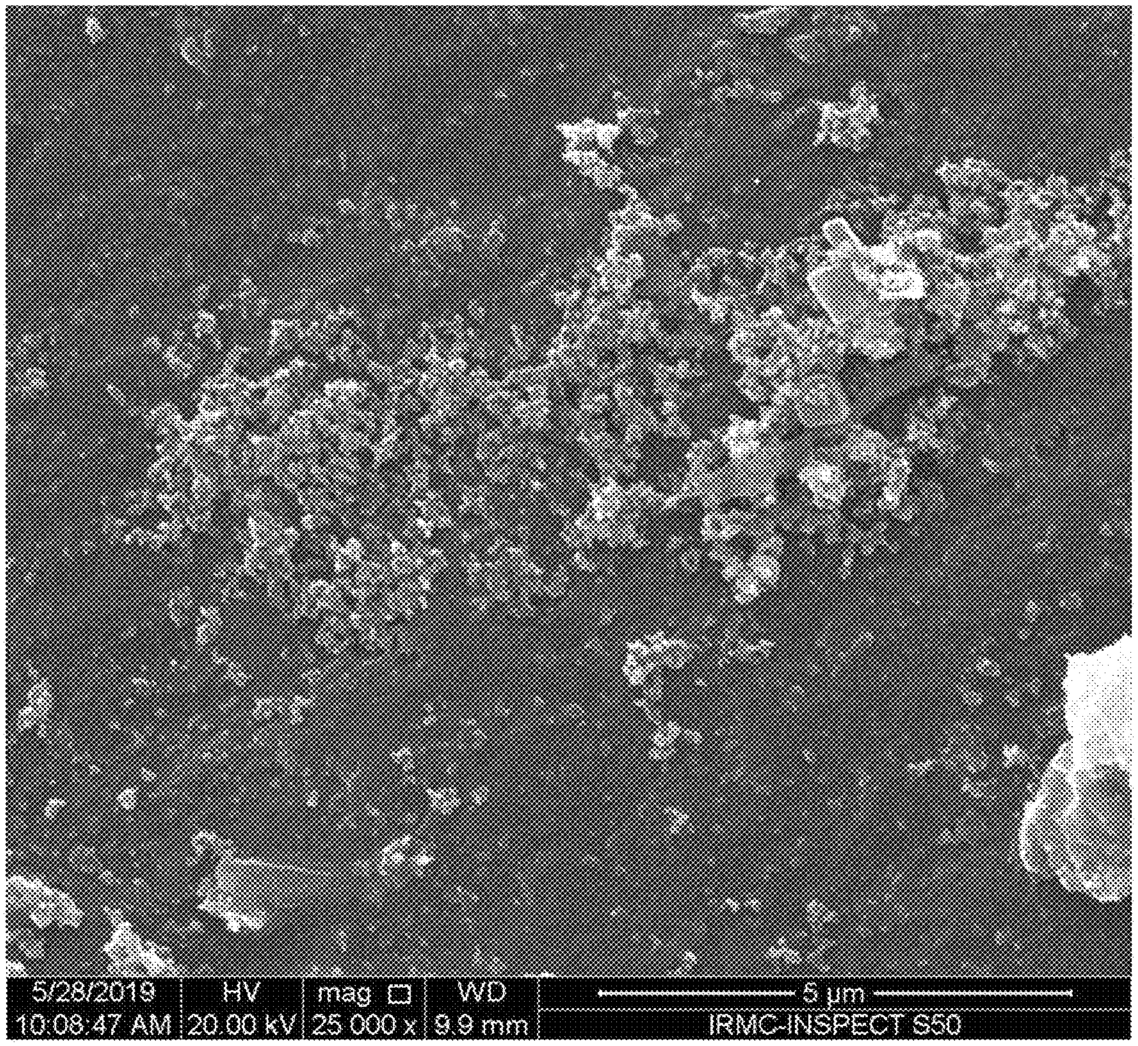
Figure 3H:
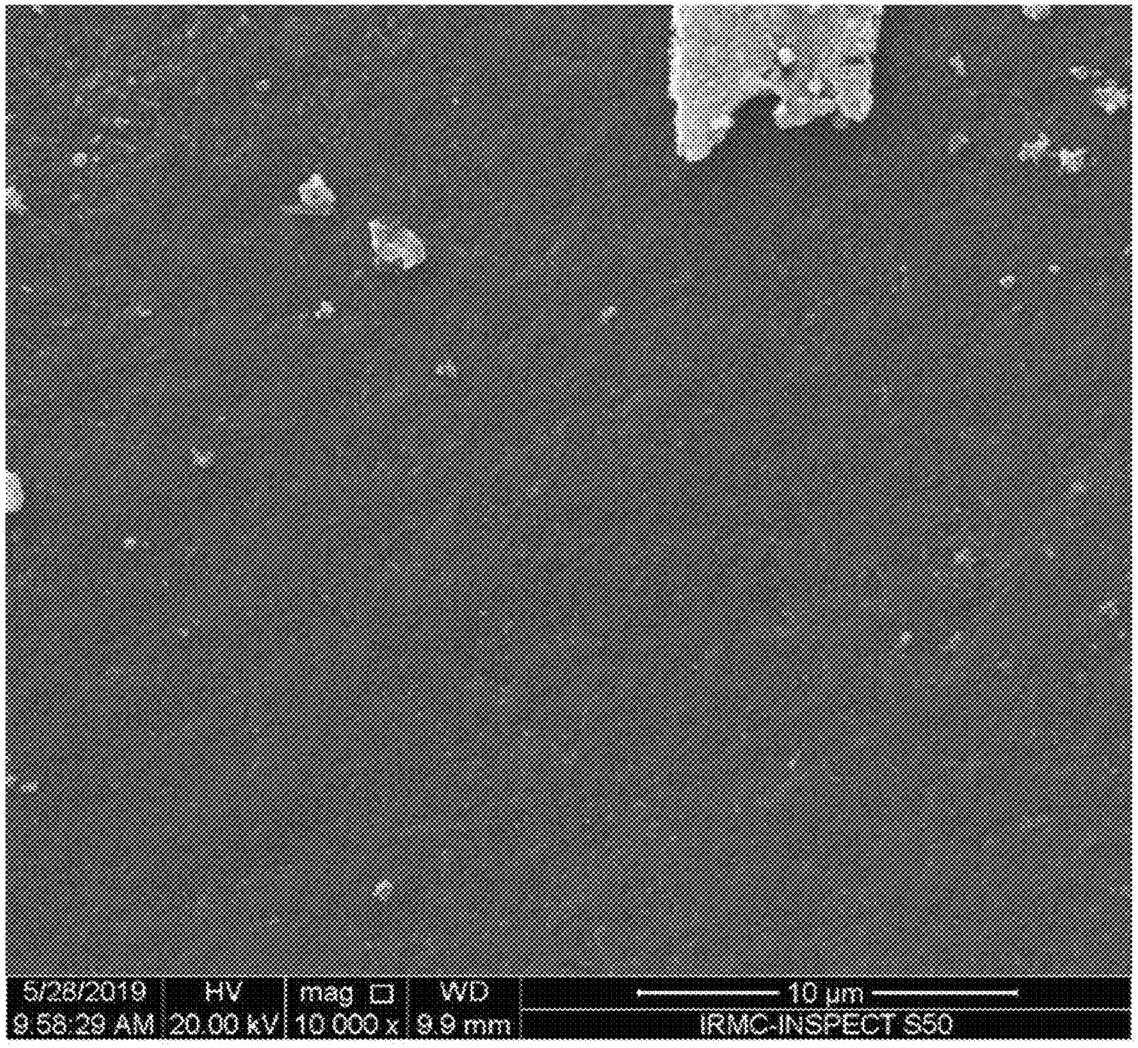
Figure 3I:
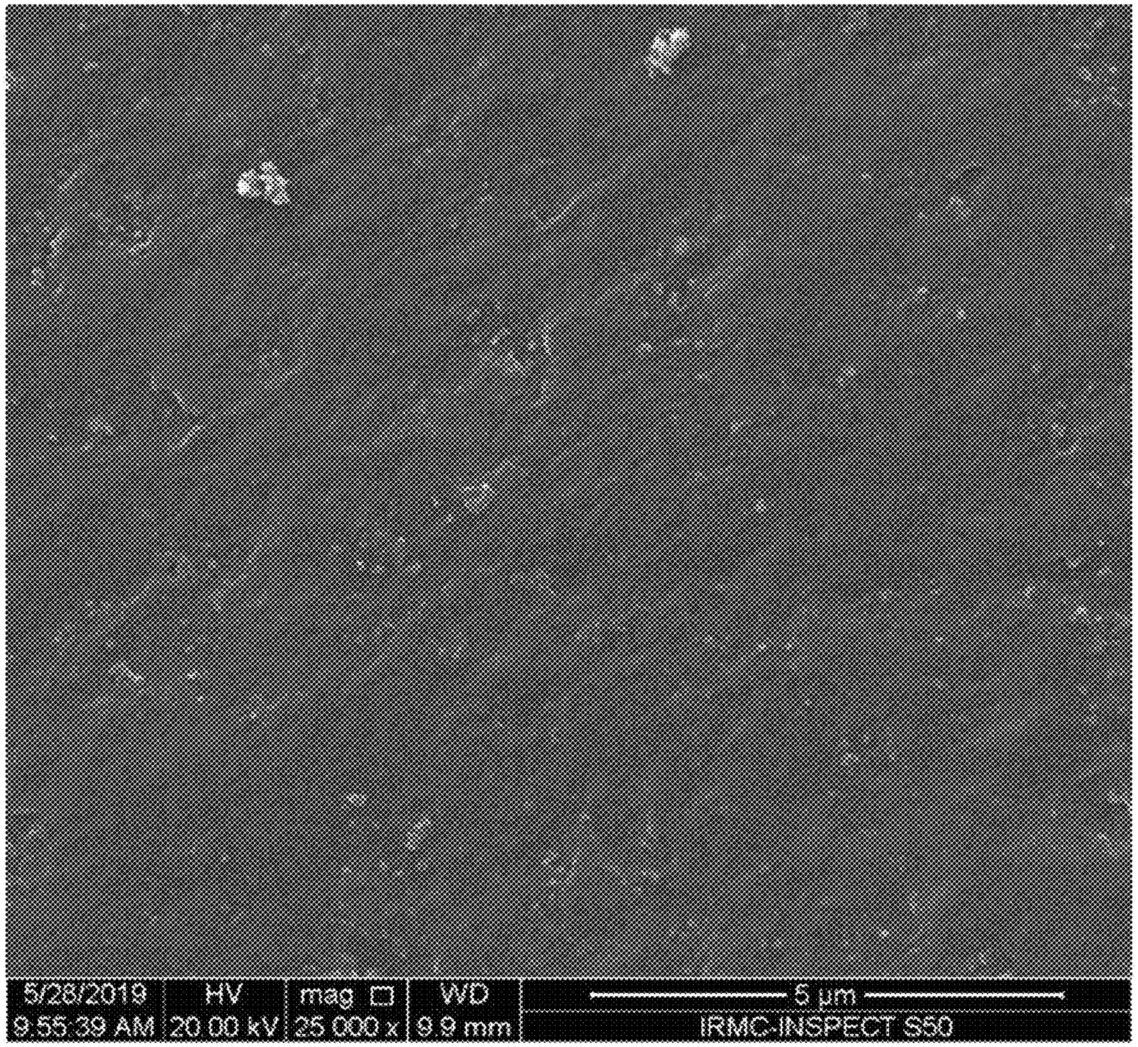
Figure 3J:
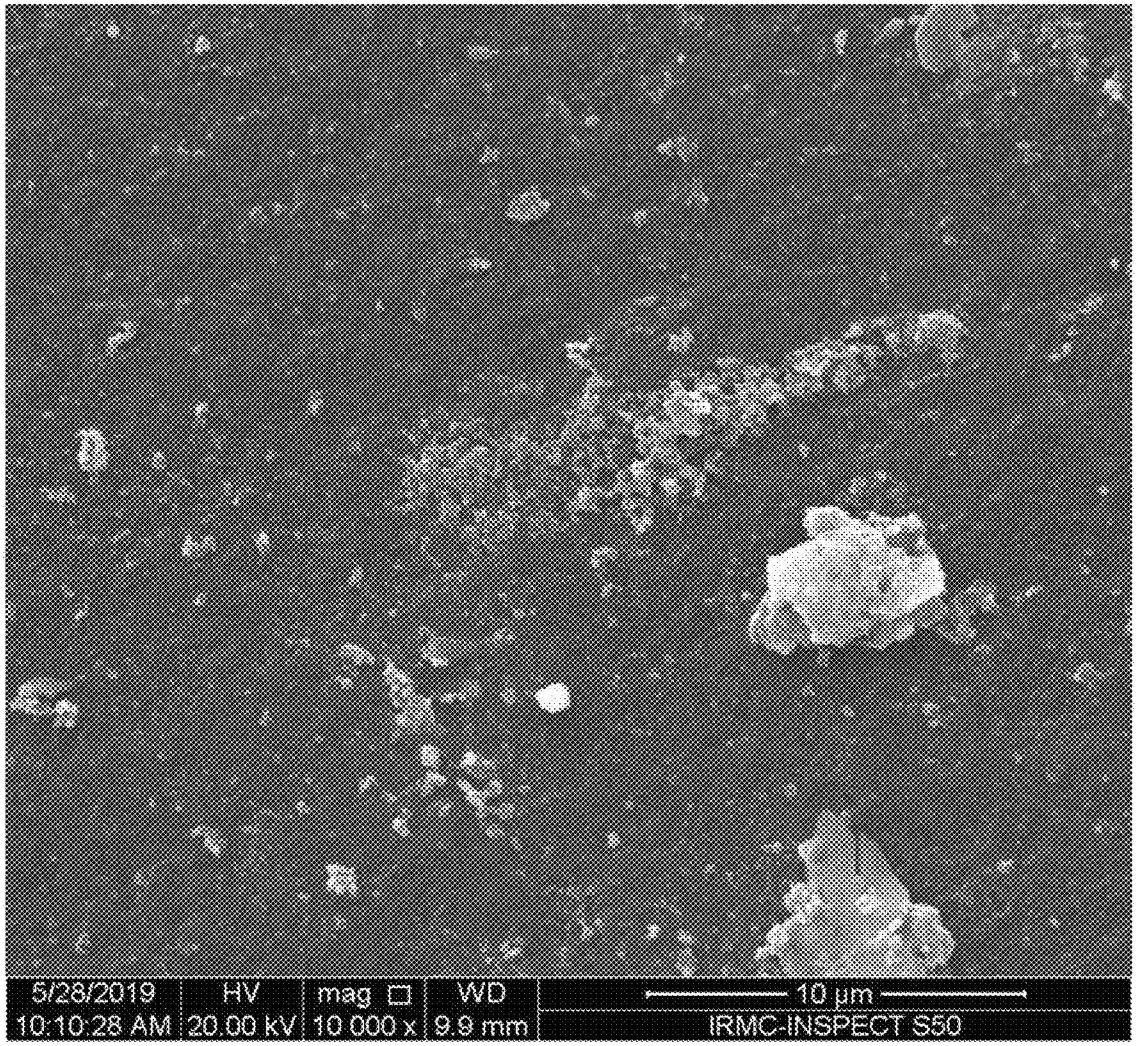

FIG. 3A to 3J show scanning electron microscope (SEM) images for exemplary nanocomposite polyethylene films coated with $TiO_2$ and Ag nanoparticles illustrating exemplary distributions on $TiO_2$ and Ag nanoparticles on large surface area on polyethylene on 5, 10, and 30 μm scale. In the SEM images, it can be seen that some surfaces have particles embedded partially in the matrix (FIG. 3A to 3*e*) while some surfaces have less surface manifestations (FIGS. 3E and 3I), some surfaces have large topological features upon the surface (FIGS. 3D, 3F, and 3H), and some surfaces have clear agglomerations of surface particles upon the surface of the matrix (FIGS. 3G and 3J).

As the weight percentage of Ag/$TiO_2$ increased, the quantity of aggregates increased and their size became more uneven and rough (round to crystal in shape). A rough surface of LDPE nanocomposites may result in better bacterial reduction by offering more sites for reactive oxygen species (ROS) release to inactivate microbes.

Figure 4A:
FIGS. 4A and 4B show photograph images of antimicrobial examinations of the polyethylene coated with $TiO_2$ and Ag nanoparticles showing antimicrobial effects with little to no evident bacterial growth.
Figure 4B:
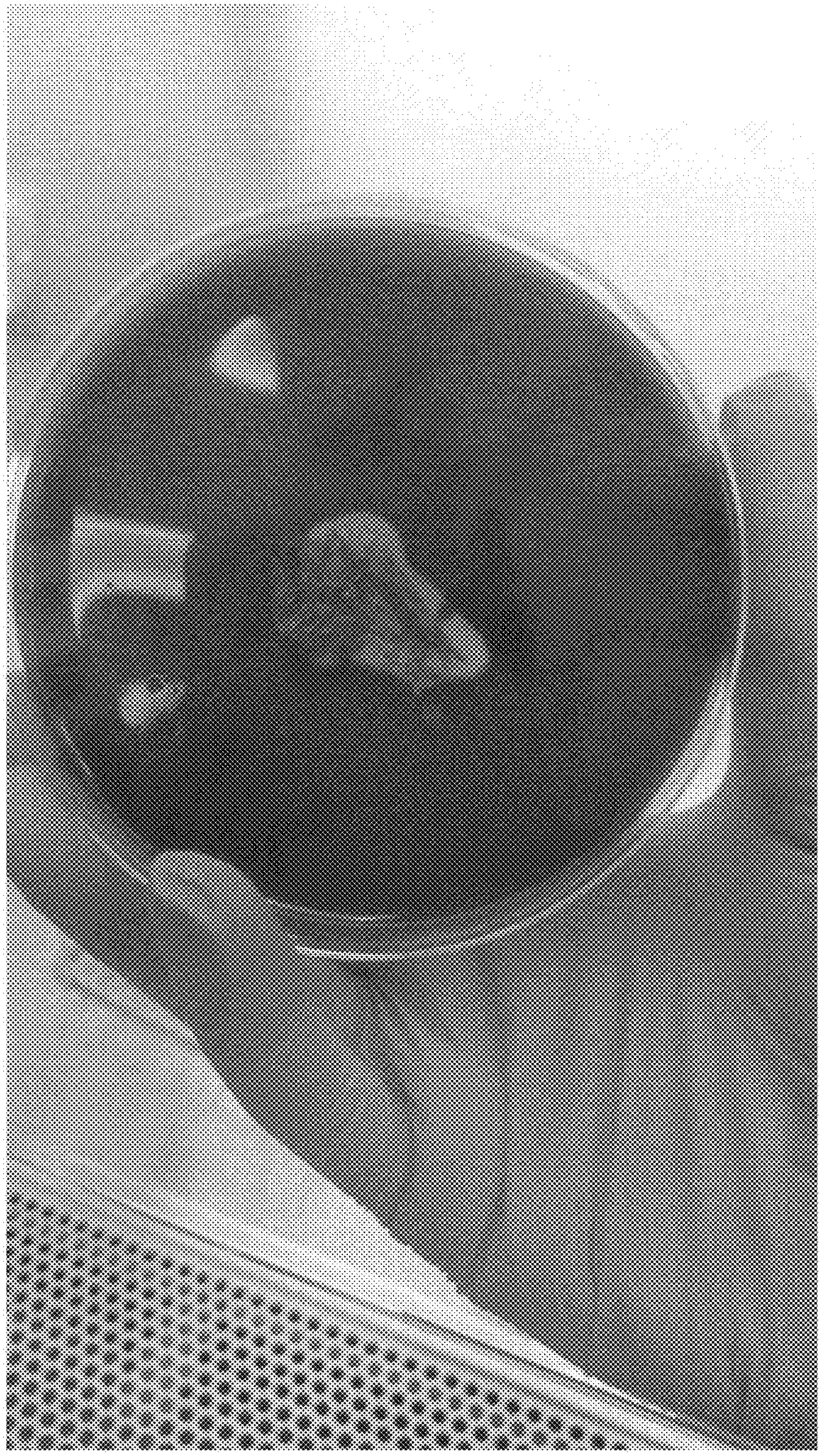

FIGS. 4A and 4B show photograph images of antimicrobial examinations of the polyethylene coated with $TiO_2$ and Ag nanoparticles showing antimicrobial effects with little to no evident bacterial growth.

Figure 5:
FIG. 5 shows an exemplary antimicrobial film/membrane with the nanocomposite polyethylene-$TiO_2$—Ag nanoparticles.

FIG. 5 shows an exemplary antimicrobial film/membrane with the nanocomposite polyethylene-$TiO_2$—Ag nanoparticles;

FIGS. 6 and 7 show a exemplary antimicrobial films/membranes in the form of a virtual reality goggle protective covers containing the nanocomposite polyethylene-$TiO_2$—Ag nanoparticles.

Numerous modifications and variations of the present invention are possible in light of the above teachings. It is therefore to be understood that within the scope of the appended claims, the invention may be practiced otherwise than as specifically described herein.

The invention claimed is:

1. A method for making a nanocomposite film, the method comprising:

dispersing and thereby mixing polyethylene, silver particles, and $TiO_2$ particles in an alcohol to form a dispersion;

drying to form a dry mixture; and melt mixing the dry mixture to form the nanocomposite film;

wherein the nanocomposite film comprises:

an organic matrix comprising at least 75 wt % of the polyethylene relative to a total weight of the organic matrix;

the silver particles; and the $TiO_2$ particles, wherein the silver particles and the $TiO_2$ particles are distributed within and/or on an outer surface of the organic matrix, wherein the silver particles have a size of 1 to 1,000 nm, and wherein the $TiO_2$ particles have a size of 1 to 50 nm.

2. The method of claim 1, wherein the nanocomposite film comprises, based on a total weight of the nanocomposite film:

1 to 5 wt % of the silver particles; and 1 to 10 wt % of the $TiO_2$ particles.

3. The method of claim 1, wherein a thickness of the outer surface of the organic matrix is in a range of from 0.025 to 25 μm.

4. The method of claim 1, wherein the polyethylene in the nanocomposite film is LDPE and is present in an amount of at least 97.5 wt % relative to the relative to the total weight of the organic matrix.

5. The method of claim 1, wherein the polyethylene in the nanocomposite film has a melting point in a range of from 90 to 125° C.

6. The method of claim 1, wherein the polyethylene in the nanocomposite film has a density in a range of from 0.9 to 0.99 $g/cm^3$.

7. The method of claim 1, wherein the $TiO_2$ particles in the nanocomposite film have an average longest dimension of no more than 25 nm, and/or wherein the $TiO_2$ particles have an average sphericity of at least 0.91.

8. The method of claim 1, further comprising:

foaming the polyethylene to form a foamed nanocomposite film wherein the polyethylene in the nanocomposite film is foamed.

9. The method of claim 1, wherein the nanocomposite film comprises no more than 2 wt % of the silver particles.

10. The method of claim 1, further comprising, prior to the dispersing:

suspending the polyethylene in the alcohol for at least 5 minutes.

11. The method of claim 10, wherein the suspending of the polyethylene takes place for up to 12 hours.

12. The method of claim 10, wherein the alcohol comprises at least 75 wt % of methanol, based on total alcohol weight.

13. The method of claim 1, further comprising, prior to the dispersing:

forming the silver particles in situ by reducing a silver precursor with a reducing agent.

14. The method of claim 1, wherein the melt mixing comprises heating at a temperature in a range of 10% of a melting point of the polyethylene, and/or wherein the melt mixing comprises heating at a temperature in a range of from 100 to 115° C.

* * * * *